(12) United States Patent
Geiger et al.

(10) Patent No.: US 9,103,838 B2
(45) Date of Patent: Aug. 11, 2015

(54) APPARATUS AND METHODS FOR SEPARATING AND ANALYZING COMPONENTS IN FLUIDS

(75) Inventors: Timothy Robert Geiger, Louisville, CO (US); Dean Michael Kingston, Arvada, CO (US); Steven Patrick Tyrrell, Erie, CO (US)

(73) Assignee: LYZER DIAGNOSTICS, INC., Boulder, CO (US)

( * ) Notice: Subject to any disclaimer, the term of this patent is extended or adjusted under 35 U.S.C. 154(b) by 1021 days.

(21) Appl. No.: 12/700,677

(22) Filed: Feb. 4, 2010

(65) Prior Publication Data

US 2010/0203578 A1    Aug. 12, 2010

Related U.S. Application Data

(60) Provisional application No. 61/149,769, filed on Feb. 4, 2009.

(51) Int. Cl.
*C12Q 1/02* (2006.01)
*G01N 33/72* (2006.01)

(52) U.S. Cl.
CPC .................................... *G01N 33/721* (2013.01)

(58) Field of Classification Search
CPC .................................................... G01N 33/721
See application file for complete search history.

(56) References Cited

U.S. PATENT DOCUMENTS

| | | |
|---|---|---|
| 5,135,719 A | 8/1992 | Hillman et al. |
| 6,410,341 B1 | 6/2002 | Freitag et al. |
| 7,115,421 B2 | 10/2006 | Grzeda et al. |

FOREIGN PATENT DOCUMENTS

WO    WO 2006017703    *    2/2006    ............. B01D 29/00

* cited by examiner

*Primary Examiner* — Laura Schuberg
(74) *Attorney, Agent, or Firm* — Peter B. Scull; Hamilton, DeSanctis and Cha, LLP

(57) ABSTRACT

Provided are methods and devices for separating particulate analytes or aggregates of analytes from a fluid, after the separation medium of the device is saturated with the fluid. The endpoint indicating completion of the separation is determined by saturation; therefore, no precise metering of the fluid sample is necessary. The separated analyte of interest can be detected, quantitated or its migration measured in the separation medium. The measured property of the analyte can then be correlated with a parameter of interest. In some embodiments, the device can be marked to directly read the value of the parameter of interest. In one embodiment, the fluid is blood and the device includes a volumetric capillary reservoir for collecting the blood, a separation paper or indicator strip, and graduations for correlating the migration of red blood cells with hematocrit or hemoglobin concentration. The interface of red blood cells and plasma creates a readable marking that corresponds to percent hematocrit and can be read from the graduations.

11 Claims, 5 Drawing Sheets

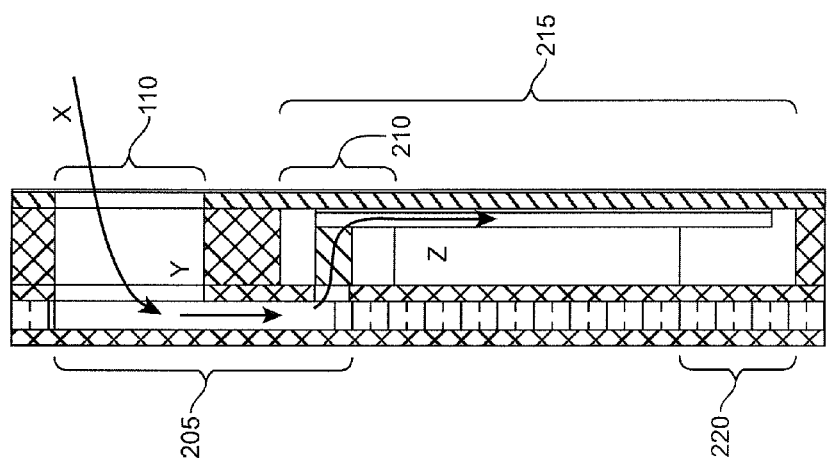
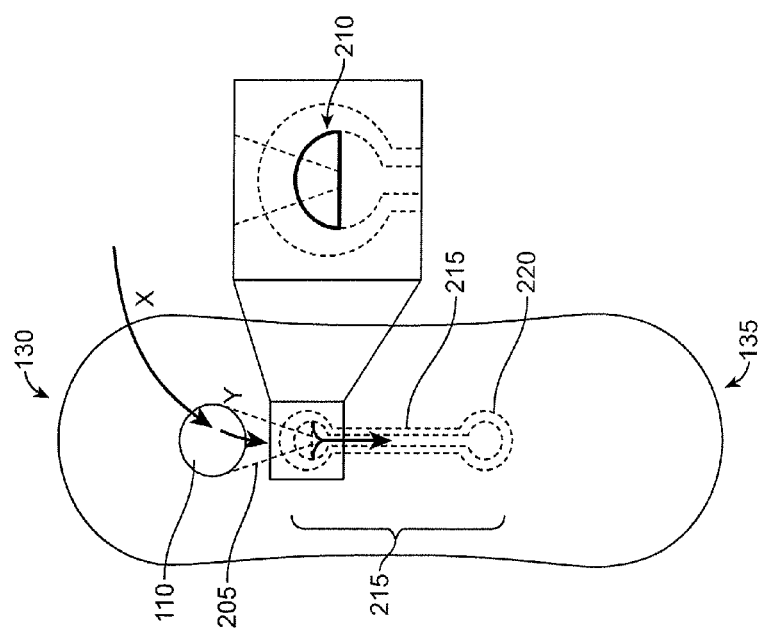

APPARATUS AND METHODS FOR SEPARATING AND ANALYZING COMPONENTS IN FLUIDS

RELATED APPLICATIONS

This application claims priority under 35 U.S.C. §119(e) to U.S. Provisional Application Ser. No. 61/149,769 entitled "A LOW-COST DISPOSABLE DEVICE FOR TESTING HEMATOCRIT AND HEMOGLOBIN LEVELS" filed Feb. 4, 2009. The subject matter of the provisional application is incorporated in its entirety by reference herein. This application also is related to International PCT Application No. (PCT/US2010/023246) filed on the same day herewith. The subject matter of the PCT application is incorporated by reference herein.

FIELD OF THE INVENTION

Device and method for measuring parameters associated with the migration of an analyte through a separation medium. In one embodiment, the method and device provided herein measures hematocrit or hemoglobin in whole blood by separating the red blood cells from plasma using a blood separation paper-based medium.

BACKGROUND

The use of rapid on-site testing to assess a condition, situation or problem arises in a number of areas such as diagnostics, environmental monitoring and testing, monitoring of physical, biological or chemical phenomena (such as the formation of physical aggregates of particles or aggregation due to chemical forces, such as protein-protein interactions), water contamination and food contamination. Current methods and devices available for such testing are often costly and cumbersome to use at the point of care or at the site of interest, due to the need for precise metering of the sample to be tested. Accordingly, there is a need for cost-effective, compact, rapid testing devices that eliminate the difficulty of having to measure precise, reproducible amounts of a sample that is to be tested on site. In one application, a simple, low cost, at-home device for testing blood hematocrit can be of significant benefit to patients with anemia, given the cost of other devices on the market that require an electronic meter.

SUMMARY

Provided herein are methods and devices designed to separate and detect the presence, the relative amount or the relative migration in a separation medium of analytes in fluids such as blood, milk, water, solutions containing biological molecules such as proteins and nucleic acids, and biological fluids other than blood such as plasma, serum, urine, saliva, seminal fluid, lavages, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum or fractions or components thereof. The analytes can be particulates that are present as a suspension or colloid in the fluid; alternatively, the analytes can be dissolved in the fluid as a homogeneous solution and are detected upon their transformation (e.g., aggregation or complexation with a binding partner) to form particulates. The detection, relative amount, or relative migration of the analyte is associated with a parameter that can be used to analyze the cause or nature of a condition, situation or a problem.

The devices provided herein can achieve separation of a number of configurations of analyte, including: particulate analytes from liquid components of a fluid, smaller particulate analytes from larger particulate analytes, and differing degrees of aggregation of the same analyte. In some embodiments, detection labels or dye indicators can be used to monitor the method and/or to detect the analyte or aggregation stage of interest.

The methods and devices provided herein can analyze and/or monitor a number of processes including protein-protein interactions, nucleic acid hybridization, small molecule binding, response to an enzymatic reaction, or changes in characteristics of the media, such as pH, salt levels and protein concentration. The methods and devices provided herein can assess the presence, relative amount, or relative migration in a separation medium of particulate analytes or analytes that undergo aggregation such as cells in blood and other biological fluids, particulates in colloidal suspensions such as milk, particulates in water, pigments in ink, paint and other such suspensions; bacteria, yeast, or other microorganisms in water, food samples and biological fluids. The assessment can then be correlated with a parameter, such as water contamination or a medical diagnosis. For example, when the fluid is blood, the migration of red blood cells through a separation medium according to the methods and devices provided herein can be correlated with hematocrit, which can be used to determine whether a subject is anemic. The methods and devices provided herein are designed to be employed at the point of care, such as in the home, in hospital emergency rooms or operating rooms, hospital laboratories and other clinical laboratories, doctor's offices, in the field, or in any situation in which a rapid and accurate result without the use of a cumbersome, expensive device is desired. In some embodiments, the device provided herein is disposable.

In one embodiment, provided herein is a disposable, low-cost point-of care device that provides accurate measurements of hematocrit. A method and device for visualizing hematocrit in a blood sample are provided. The method includes the process by which administered blood is exposed to heparin to prevent clotting then separated through a vertical separation paper and focused onto a graduated Indicator Strip that correlates migration distance of the separated blood cells with hematocrit. Blood is not metered prior to migration onto the blood separation paper. The blood separation paper achieves saturation and this arrests any further migration of the blood along the separation strip. Migration of the blood takes less than 15 minutes and can be read once saturation of the strip has been reached. The device includes an indicator at the distal portion of the test strip that indicates to the user that the blood has migrated the entire distance of the test strip meaning that the test was successful. In addition, the device embodies an indicator at the proximal portion of the test strip to indicate to the user when sufficient blood has been added.

Provided herein is a method for determining the proportion of a particulate analyte in a fluid that includes:
applying the fluid to a proximal end of a substrate, where the substrate provides for differential migration of the analyte and the liquid component of the fluid in the substrate;
allowing the fluid to saturate the substrate; and
measuring the distance of migration of the analyte in the substrate relative to the proximal or distal end of the substrate, where the migration of the analyte is indicative of the proportion of the analyte in the fluid.

In some embodiments of the method, the proportion of the analyte is the volume of packed analyte relative to the volume of liquid component of the fluid. In other embodiments of the method, the proportion of the analyte is the volume of packed analyte relative to the total volume of the fluid. In yet other embodiments of the method, the proportion of the analyte is the percent weight of the analyte relative to the total volume of the fluid. In further embodiments, the proportion of the analyte is the percent weight of the analyte relative to the total weight of the fluid.

In one embodiment of the method, the amount of fluid analyzed by the substrate is not measured or metered prior to introducing the fluid into the substrate, i.e., an unknown amount of fluid is loaded onto and migrates in the substrate. In another embodiment, the distance of migration of the analyte in the substrate is measured relative to the proximal end of the substrate.

In one embodiment of the method, the fluid that is analyzed by the method is blood. The particulate analyte of interest whose migration is measured according to the method provided herein can be any component of blood, such as white blood cells, red blood cells or blood platelets. In some embodiments, the particulate analyte of interest is red blood cells.

The method provided herein can include a further step of correlating the migration of the analyte to a parameter associated with the migration of the analyte in the substrate. The parameter, used interchangeably with "assessment parameter" herein, is a property that is indicative of the cause or nature of a condition, situation or problem and can be used to diagnose or monitor the condition, situation or problem. In an exemplary embodiment, the fluid that is separated by the substrate is blood, the particulate analyte is red blood cells and migration of the red blood cells in the substrate is correlated to an assessment parameter (or, in this instance, "blood parameter" associated with the migration of the red blood cells in the substrate. In one embodiment, the blood parameter is hematocrit, i.e., the packed red blood cell volume relative to plasma volume. In another embodiment, the parameter is hemoglobin concentration.

In any of the methods described above, one embodiment can include a substrate that is a strip. In some embodiments, the strip is made of a glass fiber filter. In yet other embodiments, the proximal and distal ends of the strip are wider than the midsection of the strip. In further embodiments, the strip is shaped like a dumbbell.

In any of the methods described above, the dimensions of the proximal and distal ends of the substrate can be are adjusted whereby, upon saturation, migration of the particulate analyte of interest is measured in the midsection of the strip. In some embodiments, the migration is adjusted to a particular, predetermined value. In yet other embodiments, the strip is shaped like a barbell or dumbbell. In further embodiments, the fluid is blood and the particulate analyte of interest is red blood cells.

Also provided herein is a method of setting the extent of migration of component(s) of a fluid in a substrate to a predetermined value(s) that includes:

preparing or obtaining a substrate for separating particulate component(s) of the fluid from liquid component(s) of the fluid, where the proximal and distal ends of the substrate are wider than the midsection of the substrate; and adjusting the dimensions of the ends of the substrate relative to each other and/or to the midsection of the substrate, where the migration of the component(s) of the fluid in the substrate is/are set to a predetermined value(s).

In some embodiments, the predetermined value of migration of a particulate component of the fluid is measured in the midsection of the substrate. In other embodiments, the migration of the particulate component in the substrate is indicative of the proportion of the particulate component in the fluid relative to the liquid component of the fluid. In any of the embodiments of the method, the substrate can be saturated with the fluid.

In some embodiments of the method, the migration of the particulate component is associated with a parameter. In other embodiments of the method, the fluid is blood, the particulate component is red blood cells and the parameter is hematocrit. In yet other embodiments, the dimensions of the ends of the substrate relative to each other and/or to the midsection of the substrate are adjusted according to the range of hematocrit values to be determined by measuring migration of the particulate analyte of interest, one embodiment being red blood cells from blood, in the substrate.

Also provided herein is a method of determining hematocrit that includes:

applying blood to a proximal end of a substrate, where the substrate provides for differential migration of the red blood cells and the plasma from the blood in the substrate;

allowing the blood to saturate the substrate; and determining the position of migration of the red blood cells in the substrate relative to the proximal or distal end of the substrate, where the position of migration of the red blood cells is directly proportional to hematocrit.

In some embodiments of the method, the blood is obtained from a subject, a particular embodiment being a human subject. The blood can applied directly from the subject onto the substrate, or can be collected from the subject prior to being applied to the substrate. In some embodiments, the blood is from a stored container. The method can be performed by collecting a fluid sample from the subject in the home, in a hospital emergency room, in a hospital operating room, in a hospital laboratory, in a clinical laboratory, in a doctor's offices or in the field. In some embodiments, an unknown amount of the blood is applied to the substrate. In other embodiments, the position of migration of the red blood cells in the substrate is determined relative to the proximal end of the substrate.

In some embodiments of the method for determining hematocrit, the substrate is a strip. In further embodiments, the strip is a glass fiber filter strip. In yet other embodiments, the proximal and distal ends of the strip are wider than the midsection of the strip. In some embodiments, the strip is shaped like a dumbbell or barbell. In other embodiments, the dimensions of the proximal and distal ends of the dumbbell are adjusted whereby, upon saturation, the position of migration of the red blood cells is in the midsection of the strip.

Also provided herein is a method for determining the extent of aggregation of an analyte in a fluid that includes:

applying the fluid to a proximal end of a substrate such that when the analyte is aggregated, the substrate provides for differential migration of aggregated analyte and the liquid component of the fluid in the substrate;

allowing the fluid to saturate the substrate; and measuring the distance of migration of the aggregated analyte in the substrate relative to the proximal or distal end of the substrate, where the migration of the aggregated analyte is indicative of the proportion of the analyte that has aggregated in the fluid.

In some embodiments, prior to applying the fluid to the proximal end of the substrate, a binding partner is added to the substrate whereby the binding partner causes aggregation of the analyte. In other embodiments, prior to applying the fluid to the proximal end of the substrate, a binding partner is added to the substrate whereby the binding partner inhibits aggregation of the analyte.

Also provided herein is a device for separating components of a fluid that includes:

a lateral strip having a first end, a second end, and an elongated middle section connecting the first end and second end and forming a fluid pathway for fluid to flow from the first end toward the second end, the test strip configured to separate a particulate component of a fluid from a liquid component of the fluid;

where the first end and second end are of wider dimensions than the middle section.

In some embodiments, the device further includes a housing that at least partially contains the lateral strip, and further contains:

a first layer above the lateral strip; and a second layer below the lateral strip, where the first and second layers compress the lateral strip therebetween.

In other embodiments, the lateral strip is dumbbell shaped. In yet other embodiments, the device further contains:

a well for receiving an amount of fluid;

a capillary reservoir that provides a fluid pathway between the well and the first end of the test strip via a vertical separator; and an excess volume reservoir that is configured to receive and collect an excess volume of fluid from the second end of the test strip.

In some embodiments, the device further contains a graduated scale configured to provide an indication as to migration of a component of the fluid through the substrate. In other embodiments, the indicator strip is dye-free. In yet other embodiments, the device further contains a dye-indicator at the second end of the test strip. In further embodiments, the device contains an indicator that indicates when a sufficient amount of fluid has been added to the device.

As would be apparent to one of skill in the art, the methods and devices provided herein include any and all permutations and combinations of the ingredients, steps and/or parameters described.

BRIEF DESCRIPTION OF THE DRAWINGS

FIG. 2 shows a top view of the device with a top cover removed.

FIG. 3 shows a side, cross-sectional view of the device.

DETAILED DESCRIPTION

A. Definitions

Figure 1:
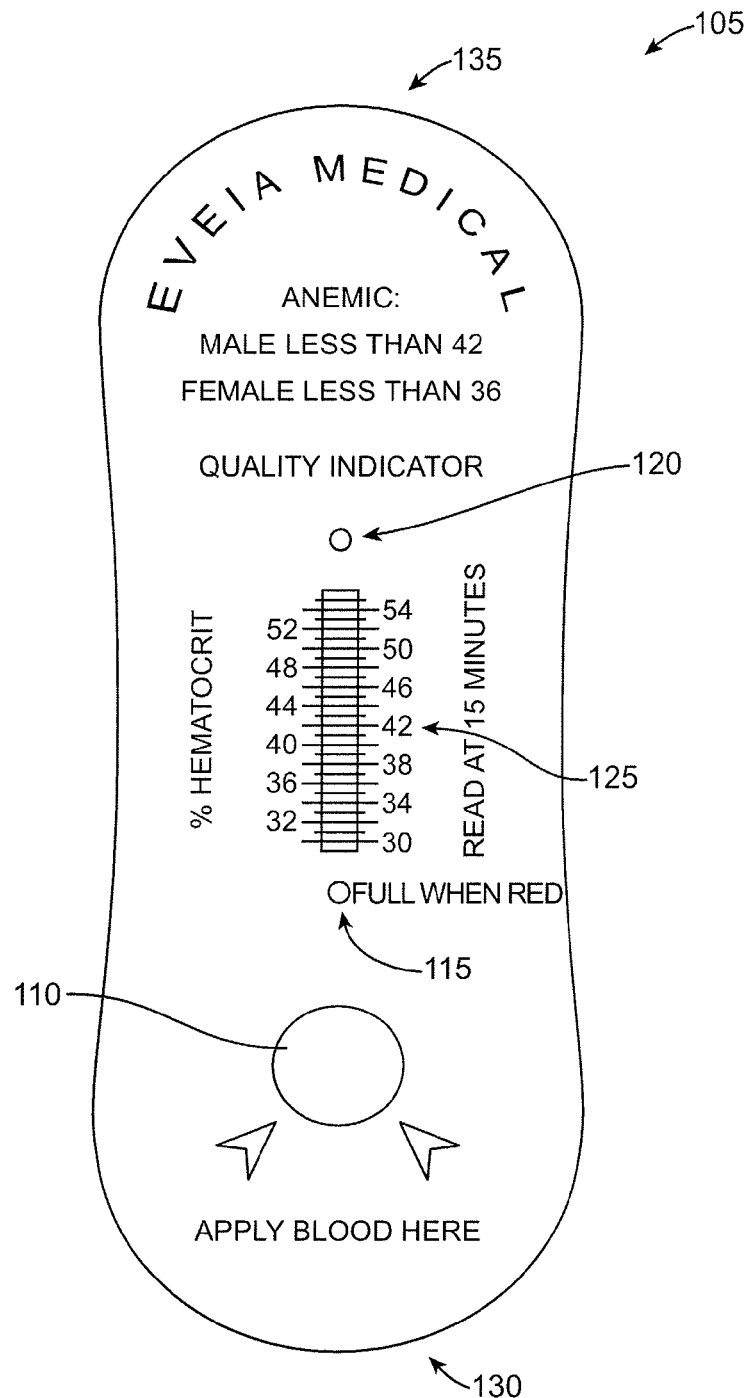
FIG. 1 shows a top view of an exemplary embodiment of the device.

Unless defined otherwise, all technical and scientific terms herein have the same meaning as is commonly understood by one of skill in the art to which the invention(s) belong. All patents, patent applications, published applications and publications, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the Internet. Reference thereto evidences the availability and public dissemination of such information.

The term "fluid" as used herein generally refers to a solution, a liquid suspension or a colloidal suspension, including a sol, although the term could also refer to any composition that is fluidizable, whether liquid, solid or gas. "Fluidizable" means a property that renders the ability to "flow," or be "deformable," i.e., the ability of a substance to be poured and to assume the shape of a container that it is poured into without hindrance. A "liquid suspension" is used interchangeably with "suspension" herein and refers to a system in which solid particles, often only microscopically visible such as red blood cells in blood, are dispersed throughout a less dense liquid from which they can be filtered but are not easily settled due to system viscosity or molecular interactions. A "colloidal suspension" as used herein refers to a suspension in which the solid particles are dispersed evenly throughout the liquid.

The term fluid as used herein can also refer to solutions. The term "solution" as used herein refers to a homogeneous mixture of two or more ingredients in a single phase, generally liquid but can also be a frozen liquid or gas, where the distinct ingredients only are recognizable at the molecular level. For example, the methods and devices provided herein can be used to monitor the aggregation of an analyte of interest, where the analyte is initially in solution but forms solid particles upon aggregation.

Exemplary fluids that can be used in the methods and devices provided herein include, but are not limited to, fluids such as blood, milk, water, solutions containing biological molecules such as proteins and nucleic acids, and biological fluids other than blood such as plasma, serum, urine, saliva, seminal fluid, lavages, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum or fractions or components thereof. The analytes can be particulates that are present as a suspension or colloid in the fluid; alternatively, the analytes can be dissolved in the fluid as a homogeneous solution and are detected upon their transformation (e.g., aggregation or complexation with a binding partner) to form particulates. The fluid sample collected can be taken from any source, as provided herein or otherwise known in the art. Fluid samples (e.g., blood) can directly be applied from a subject onto the device provided herein, or they can be collected and/or stored prior to loading onto the device.

The term "internal forces," as used herein, refers to forces that can affect movement of fluid in a separation medium that are provided by the materials and/or the design of a system that includes a separation medium for the flow of fluid therethrough. Internal forces include, but are not limited to, capillary action, wicking, bulk flow and pressure differentials. Thus, internal forces are forces inherent in a system or device and are distinct from external forces, such as gravity and forces supplied by pumps, that are not generated by the materials and/or design of a separation medium-containing system.

The term "internal influences," as used herein, refers to influences that can affect movement of fluid in a separation medium that are inherent to the fluid and/or the system that includes a separation medium for the flow of fluid therethrough. Internal influences include, but are not limited to, diffusion, chemical or biological reactions, interparticle and particle-medium adhesion.

The term "bulk flow," as used herein, refers to a property of the movement of fluids and components thereof in which the movement of fluids due to forces such as capillary forces entrains components of the fluid and causes them to flow.

The term "absorptive capacity," as used herein, refers to a measure of the quantity of liquid a material can hold. It is reported on either an area basis (e.g., gm of liquid per square meter of material) or a weight basis (e.g., gm of liquid per gm of material)."

The term "absorption," as used herein, refers to the process whereby atoms, molecules or ions enter or permeate a bulk phase (e.g., liquid, gas or solid) and are taken up by the volume of the phase.

The term "adsorption," as used herein, refers to the adhesion of molecules to a surface referred to as the adsorbent. A variety of forces of varying strengths can promote such adhesion, including but not limited to, van der Waals forces, electrostatic interactions and chemical bonds, e.g., ionic and covalent bonds.

The term "blood components", as used herein, refers to red blood cells, platelets, white blood cells, plasma, serum and any other component that is naturally present in blood or can be obtained from blood.

The term "parameter," used interchangeably herein with "assessment parameter," refers to a property associated with a particulate analyte (or aggregate) analyzed by the methods and devices provided herein. The property can be used to identify and/or monitor the cause or nature of a condition, situation or problem. For example, the detection of blood in urine can be used to diagnose and/or monitor a disease, such as kidney disease. The term "blood parameters" as used herein refers to a property that is associated with a particulate analyte (such as red blood cells, white blood cells or platelets) present in blood that can be used to identify and/or monitor a blood-related disease or other disease. Exemplary blood parameters include hematocrit and hemoglobin concentration.

The term "hematocrit" as used herein refers to the percentage by volume of packed red blood cells after the blood has been processed, such as by centrifugation to separate the red blood cells from the plasma. The term "hematocrit", as used herein, is considered equivalent to and linearly related to "hemoglobin concentration" (3% hematocrit approximately equals 1 g/dL of hemoglobin). Therefore, all references to hematocrit within this document also refer to hemoglobin concentration and the device provided herein both hematocrit and hemoglobin concentration. Both these blood parameters can be used to identify and monitor disease conditions, such as anemia.

The terms "separation medium," "separation media," "separation substrate" or "substrate that provides for differential migration" of components of a fluid are used interchangeably herein, and refers to any material through which movement of at least one, more than one, at least two, two or more, or all of the component parts of a fluid mixture can occur. The movement of the fluid component or components in the medium or media is such that the component(s) of interest for which separation from the other components is desired occurs at a different rate(s) than the other component(s), thereby effecting separation of the desired component(s). In particular methods and devices for separating components of a fluid mixture provided herein, the separation medium is a solid material. In methods provided herein wherein the fluid mixture is an aqueous fluid mixture, the separation medium is a hydrophilic material. "Differential migration" as defined herein refers to the different rates at which the solid and liquid components of a fluid migrate in the separation medium.

The term "liquid component" of a fluid refers to the portion of the fluid that remains after substantially all the solid component(s) of interest, or particulate analytes, have been separated from the fluid. Thus, the liquid component of a fluid, as used herein, can include solid particles in suspension but they generally are not the analyte(s) of interest. For example, if the fluid is blood and the device provided herein separates the red blood cells from the blood, the plasma could contain a few suspended cells and/or other particulates and still be considered as the liquid component.

The term "solid component," used interchangeably with "particulates" or "particulate analyte" refers to solid particles of interest in a fluid, analyzed according to the methods and devices provided herein, which are associated with a parameter to be identified or monitored. In some embodiments, the solid particle of interest is an aggregate of an analyte that is originally in solution in the fluid and forms a solid particle suspended in the fluid upon aggregation. The term "solid particle" as used herein can refer to particles in the size range (average length, width or diameter) of about or at 0.001 micron ($\mu$m) to about or at 500 microns, but generally are in the range of about or at 0.5 micron to about or at 1.0, 2.0, 3.0, 4.0, 5.0, 6.0, 7.0, 8.0, 9.0, 10.0, 15.0, 20.0, 25.0, 30.0, 40.0 or 50.0 microns.

The term "agglomerates" refers to the association of one or more particles, such as particulate analytes, loosely held together by van der Waals forces or surface tension or electrostatic or combinations thereof. In some instances, associations held by electrostatic forces can be defined as "Flocculates." For the purposes herein, "agglomerates" also encompasses "Flocculates".

The term "aggregates" refers to the association of one or more particles, such as particulate analytes or analytes in solution, to form larger solid particles (or, if the analyte was originally in solution, particles). Aggregates generally are not easily broken apart, which inhibits their migration in a separation medium and allows the process of aggregation to be monitored.

The phrase "proportion of a particulate analyte in a fluid" can refer to more than one property, depending on the parameter that is associated with the particulate analyte of interest. For example, it can refer to the volume of packed particulate analyte (fractional volume) relative to the volume of liquid component of the fluid, the volume of packed analyte (fractional volume) relative to the total volume of the fluid (or "fractional volume"), the percent weight of the analyte relative to the total volume of the fluid, or the percent weight of the analyte relative to the total weight of the fluid.

As used herein, a "detectable label" or moiety or an imaging label or moiety refers to moieties used to image a particulate analyte of interest. Such moieties include, for example, fluorescent moieties, radionuclides, magnetically detectable isotopes or compounds, sonographic imaging agents, chromophores, latex microspheres, or quantum dots.

As used herein, a "binding partner" is a compound that specifically binds to a particular molecule or class of molecules (analyte(s) of interest). Binding partners as used herein bind to analytes and can, in some embodiments, promote or inhibit the formation of particle aggregates. Types of binding partners can include beads, proteins, nucleic acid molecules, carbohydrates, lipids, ligands, drugs, ions and any other compound that can specifically bind to a particular molecule.

As used herein, the term "proximal end" refers to the end of the device or component of the device (such as the indicator strip) that is closer to the point at which the fluid sample is loaded onto the device.

As used herein, the term "distal end" refers to the end of the device or component of the device (such as the indicator strip) that is farther from the point at which the fluid sample is loaded onto the device.

As used herein, the term "midsection" or "middle section" in general refers to the portion of the indicator strip of the device, flanked by the proximal and distal ends, on which the migration, detection, aggregation or other property of the analyte is measured.

As used herein, reference to a housing that "at least partially" covers the indicator strip or any other component of the device means that at least 10% of the device is covered.

As used herein, the term "dimensions" refers to shape, length, width and area

As used herein, the term "saturation" or "saturated" refers to a condition, point or stage where no more of the liquid or fluid medium can be absorbed or adsorbed by the substrate (e.g., the separation medium).

The term "diffusion," as used herein, refers to movement of a fluid from an area of high concentration to an area of low concentration.

The term "adhesion" or "adhesive forces," as used herein, refers to the intermolecular attraction between unlike molecules. One example of adhesion is the intermolecular attraction between fluid molecules and the walls of a glass tube containing the fluid.

The term "capillary action" or "capillary force," as used herein, refers to the force that results from adhesive forces and surface tension acting on a fluid in a small passage or vessel, such as a tube, which serves to move a fluid through the vessel. When the adhesive force generated by intermolecular attraction between fluid molecules and the walls of a vessel in which the fluid is contained is stronger than the cohesive forces within the fluid resulting from intermolecular attraction between the fluid molecules, an upward force on the fluid at the edges of the vessel results. This force pulls the fluid at the vessel edges upward resulting in a meniscus. At the same time, surface tension generated by the enhanced cohesive forces between fluid molecules at the surface of the fluid acts to hold the surface intact resulting in the upward movement of the entire fluid surface and not only the edges of the fluid surface. This combination of forces is referred to as capillary force or action.

The term "wicking" or "wicking forces," as used herein, refers to the movement of fluid through a porous medium as a result of capillary forces occurring in the pores of the medium. Typically, a porous medium has some degree of capillarity to the extent that fluid moves through the medium due to capillary forces created by, for example, small diameter pores or the close proximity of fibers.

The term "meter" as used herein with reference to an action performed on a fluid sample, such as, for example, blood, refers to measuring a known amount of the fluid and analyzing a known amount of fluid loaded into a separation medium.

B. Methods for Separating Components of Fluids

Provided herein are methods for separating components of a fluid mixture. The methods include application of a fluid mixture to a separation medium or media in order to effect separation of fluid components based on differential movement of components in the medium or media. Because a component is physically separated in the medium from one or more other components in the mixture, the methods make possible the detection of a component of a mixture. For example, the separated component can be detected through either direct observation or measurement of an inherent property (e.g., color) of the component or through observation/measurement of a detectable label specific for the component (indirect detection). Accordingly, also provided herein are methods for detecting a component of a fluid mixture.

In particular methods of separating fluid components provided herein, the distance that a particle or solid component of the mixture travels in the medium depends on the volume of the component in the fluid. Such methods are referred to herein as fractional volume-dependent separation. Thus, not only do these methods provide for separation of a particle or solid component from a fluid mixture, they also can be used to assess the volume of the component in a fluid mixture. The distance traveled in the medium by the component can be measured and in turn used to determine the fractional volume (also referred to as percent volume, or volume-to-volume percentage), of the component relative to total volume of the fluid mixture. Accordingly, also provided herein are methods of quantifying the relative amount or fractional volume of a component in a fluid mixture.

Fluid components that can be separated in a separation medium in fractional volume-dependent manner can be identified empirically. In a particular embodiment of the methods provided herein, separation of blood components is effected based on differential movement of blood components in a separation medium or media. Using such methods, blood cells, and, in particular, red blood cells, can be separated from the liquid component, such as plasma and/or serum, through fractional volume-dependent separation. Also provided herein is a method for assessing the volume of blood cells (in particular red blood cells) in a blood sample and for determining the percent volume of the cells relative to total blood volume. The percent volume of red blood cells in blood is a measure of blood hematocrit. Thus, further provided herein is a method for determining hematocrit of a blood sample. Also provided are methods for determining the hemoglobin concentration of a blood sample. In one embodiment, the method involves using determining the hematocrit of a blood sample using the methods provided herein and using the hematocrit value thus obtained to determine hemoglobin concentration based on conversion formulas known in the art. In other embodiments provided herein for determining the hemoglobin concentration of a blood sample, the hemoglobin concentration is determined through comparison of red blood cell migration distances (or migration areas) in a separation medium saturated with the blood sample and to the migration distances or areas of red blood cells in a separation medium saturated with a blood sample with known hemoglobin concentration.

1. Fluid Mixtures and Components Thereof
   a. Components

Provided herein are methods for separating a component or components in fluid mixtures from other components, including liquids, of the fluid. The fluids can be mixtures, such as aqueous mixtures, containing particles, such as solid particles. A particular component of interest can be separated from a liquid, other smaller or larger particles and/or the same particle component in differing degrees of aggregation. The component(s) to be separated within or from the fluid are particles that are not dissolved in the fluid; thus, the particles are generally of a size that is larger than the molecular or ion level. For example, the particles typically are at least 1 nanometer in size or larger than 1 nanometer. Particle sizes include, for example, sizes of 2 or more nanometers, 1-5 nanometers, 1-10 nanometers, 1-100 nanometers, 5-200 nanometers, 1-500 nanometers, 1-1000 nanometers, 100-500 nanometers, 500-1000 nanometers, at least 1000 nanometers, 1000 nanometers or more, or greater than 1000 nanometers, at least 1 micron, 1 micron or more, 1-5 microns, 5-8 microns, 1-10 microns, 10-50 microns, 50-100 microns, 1-100 microns, 100-150 microns in size. Upper ranges of particle size for separation from fluids in the methods provided herein can be determined empirically depending on pore size of the separation medium, and density of the particles compared to the fluid, since this can lead to sedimentation. Thus, the particles may be such that they are visible with the aid of a microscope (e.g., microscopic), a magnifying glass or with the unaided eye.

In particular embodiments, the particle is one that is about the size of a red blood cell. For example, the particle may have a diameter in the range of 6-8 microns. Exemplary particles that can be separated from mixtures using methods provided herein include, but are not limited to, cells (e.g., blood cells such as red blood cells (erythrocytes) and white blood cells (leukocytes, including agranulocytes such as lymphocytes and monocytes, and granulocytes, such as neutrophils, basophils, and eosinophils)), thrombocytes (platelets), synovial fluid cells and cancer cells, microorganisms, bacteria, yeast, pigments, particulates and aggregates of these and other particles.

In other embodiments of the methods provided herein, the particle can be a microbead, or aggregates of microbeads, that is/are coated with a substance that promotes aggregation of the microbeads. The substance can be, for example, a secondary analyte of interest or an agent that specifically binds a secondary analyte of interest (e.g., an analyte-specific antibody).

b. Fluid Mixtures

Fluid mixtures from which particle components can be separated using the methods provided herein include suspensions, colloids, sols and heterogeneous mixtures. Accordingly, particles that may be separated from other components in fluid using the methods provided herein include colloidal particles and suspended particles. Examples of fluid mixtures from which a component(s) can be separated include, but are not limited to body fluids, water samples and beverages (e.g., milk). Body fluids include native body fluids which are taken from or excreted by the body (e.g., of an animal, including mammals and, in particular, humans) and non-native liquids, in particular wash liquids, containing cells from the body, in particular from organs and body parts. Particular examples of body fluids include, but are not limited to, blood, bone marrow, cerebrospinal fluid, saliva, sweat, urine, lymph, ocular lens fluid, interstitial fluid, vaginal secretions, sputum, synovial fluid, pleural fluid, mucus, amniotic fluid, ascites, semen, feces, effusions, aspirates and wash liquids from organs (e.g., colon, lung, or bronchial lavage, bladder irrigation fluids).

In a particular method provided herein for separating components of a fluid, the fluid mixture is blood and the component that is separated from the liquid portion of blood (i.e., plasma) is blood cells, in particular, red blood cells. In further particular methods provided herein, nucleated cells (including mononuclear cells derived from blood monocytes, tissue macrophages and synovial membrane cells) are separated from synovial fluid in joints; ascitic fluid cells (such as polymorphonuclear cells and neutrophils) are separated from ascites fluid.

c. Sample Preparation and Application to Separation Media

In carrying out the methods provided herein for separating components of a fluid mixture, a sample of a fluid is applied to a separation medium. The sample may be applied directly to the medium in which components of the fluid will be resolved or applied to a separate sample receiving or delivery position that is in fluid communication with the separation medium.

The amount of sample that is applied to the medium is such that it is in excess of the absorptive capacity of the separation medium (or the combined absorptive capacities of the separation media if more than one medium is used) in order for the medium to become saturated with the fluid sample. The actual amount of the sample need not be known as long as the amount exceeds the capacity of the medium (or media). Minimal amounts of a fluid required to saturate a particular material can be determined based on the absorptive capacity of the material or can be determined empirically. Because an excess, rather than a specific, amount of sample is applied to a separation medium in the methods provided herein, it is not necessary to meter or measure precise volumes of sample. In a particular embodiment of the methods for separating blood components, sample amounts can range from about 10 µl to about 200 µl, typically between about 25 µl to about 100 µl and in one embodiment about 75 µl.

In particular embodiments of the devices provided herein for use with the methods for separating components of a fluid mixture the device includes a surface at which fluid sample can be applied to the device. The surface can be a concave depression that forms a well to receive fluid sample without loss of the sample by having it run off the device before contacting the separation medium. The sample receiving surface is in fluid communication with the separation medium or media. However, such a sample delivery well does not serve to meter or measure any particular volume of sample. Thus, the volume of sample applied to the separation medium (either directly or through fluid communication with upstream elements, such as a well), is whatever unknown amount is delivered to the device. The volume only need be sufficient to saturate the separation medium, which can be determined visually.

Depending on the fluid and/or fluid components being applied to the separation medium, the fluid sample may be treated prior to or during migration through the medium or media. Such treatments include, for example, buffers, preservatives, dyes or other materials that specifically label a particle component to facilitate detection or visualization of the component in the separation medium, and additives that promote aggregation of analytes or inhibit coagulation of components. In a particular embodiment, of the methods provided herein for separation of blood components, an anticoagulant can be added to the fluid to prevent clotting of the blood sample.

Typically, however, dyes or labels to detectably mark the liquid front of the fluid are not included in the separation medium or any other portion of the fluid pathway, or are at least excluded from the separation zone of the separation medium. This is because methods provided herein utilize the migration distance, or area of migration, of a component other than the liquid, i.e., a particle or solid component, for detection and quantitative assessment of the fluid and components thereof. The liquid migration front is not a factor that is marked because the separation medium is saturated with the liquid of the fluid. In some embodiments of the methods and devices provided herein, a dye or other label may be placed at the distal end of the medium for purposes of confirming saturation of the complete separation medium. However, such a placement does not monitor liquid front movement prior to saturation of the medium.

2. Separation of Components a. Separation Media

A separation medium is any material through which movement of at least one, more than one, at least two, two or more, or all of the component parts of a fluid mixture can occur. The movement of the fluid component or components in the medium or media is such that the component(s) of interest for which separation from the other components is desired occurs at a different rate(s) than the other component(s), thereby effecting separation of the desired component(s). In particular methods and devices for separating components of a fluid mixture provided herein, the separation medium is a solid material. In methods provided herein wherein the fluid mixture is an aqueous fluid mixture, the separation medium is a hydrophilic material.

For example, the medium can be a natural and/or synthetic material containing spaces or holes of uniform or varied sizes. The spaces can form nets or can form pores, or passages, through which some components, e.g., liquids, molecules, ions, may readily move (i.e., the medium is readily permeable to the components) but through which movement of other components is retarded or impeded due, for example, to the size and/or shape of the component. Although these other components may move through the spaces of the separation medium, the movement will be at a slower rate. Thus, the medium is less permeable to such components. Some components may be of a size and/or shape such that they are trapped in or at the entrance to the spaces and, thus, will be excluded from movement in the medium. In this case, the medium is referred to as being impermeable to that component. Other rapidly moving components may pass completely through and exit the medium. Because some components do not move in the medium and other components move at different rates through the medium, the different components are effectively separated by the medium. Media in which separation of components is based on size are referred to as size exclusion media.

Other separation media for use in the methods and devices provided herein can be natural and/or synthetic materials having properties that provide for varying degrees of interactions with different components of a fluid mixture. Such media effect separation of components in a fluid mixture due to the differential affinities of the different components of the fluid. For example, some components of a fluid mixture (e.g., liquids, molecules and ions) may have few interactions with the medium or may not interact with the medium at all. Such components are said to have little to no affinity for the medium and will move readily through the medium. Other components of the fluid mixture may interact with or weakly bind to the medium to a limited extent (i.e., with low affinity). These components will be loosely and reversibly retained in the medium and will thus move more slowly through the medium. Still other components of the fluid mixture may interact strongly (i.e., with high affinity) and/or irreversibly with the medium and will move short distances in the medium or not move in the medium at all. The interaction of a component of a fluid mixture with a separation medium may be specific for that component, such as between an antibody and antigen or a ligand and receptor, or may be non-specific. Media in which separation of components is based on differential interaction or binding of the components to the medium are referred to as adsorption-based media.

Different porous media may have pores of different sizes. The pore size of a porous medium to be used in the methods and devices provided herein is selected based on several factors, including: (1) the size of the component(s) of interest that is to be separated from other components of the fluid mixture, (2) the sizes of the other components in the fluid, (3) the extent to which it is desired to have the component of interest move or travel in the medium and (4) the separation characteristics of the component. For example, if it is desired that the component of interest move far enough in the medium to be resolved from the other components but not as far in the medium as the other components, and the component of interest is a large solid or passive particle (e.g. latex microbead or aggregate of microbeads), a suitable pore size for the medium would be one that is about the size of or slightly larger than the size of the component of interest, but significantly larger than other smaller components of the fluid mixture. On the other hand, if the component of interest is a large deformable, or otherwise active particle (e.g. a blood cell or other such cell that actively moves through small spaces) a suitable pore size for the medium would be one that is about the size of or slightly smaller than the size of the component of interest, but significantly larger than other smaller components of the fluid mixture. Such a medium would permit movement of the component of interest in the medium so that it could be detected, but would separate the component of interest from other components by retarding the movement of the component relative to the movement of the other components. Generally, the pore size will be defined by the ability of the medium to inhibit migration of the component of interest relative to the other components in the fluid, including the fluid itself. A suitable pore size for a separation medium for use in the methods and devices provided herein can be determined empirically by those of skill in this art based on the teachings of desired outcomes and particular relevant factors as provided herein.

In particular methods and devices provided herein, the separation medium is any material that has a pore size capable of separating blood cells from plasma. Although red blood cells have an average diameter of 7-8 µm, they can deform such that the diameter is decreased. Thus, for example, suitable pore sizes of the medium for particular embodiments provided herein can be 1-8 µm in diameter, 1-5 µm in diameter or, in particular embodiments, 2-3 µm in diameter. The separation medium could also be any material made of packed beads or packed or woven fibers such that the effective pore size is suitable for separating blood cells from plasma.

Examples of materials that may be used as separation media in the methods and devices provided herein include, but are not limited to natural, synthetic, or naturally-occurring materials that are synthetically modified, such as polysaccharides (e.g., cellulose materials such as paper and cellulose derivatives such as cellulose acetate and nitrocellulose and coated cellulose); polyether sulfone; polyethylene; nylon; polyvinylidene fluoride (PVDF); polyester; polypropylene; silica; inorganic materials such as deactivated alumina; diatomaceous earth; $MgSO_4$; or other inorganic finely divided material uniformly dispersed in a porous polymeric matrix with polymers such as vinyl chloride, vinyl chloride-propylene copolymer and vinyl chloride-vinyl acetate copolymer; cloth, both naturally occurring (e.g., cotton) and synthetic (e.g., nylon or rayon); porous gels such as silica gel, agarose, dextran, and gelatin; polymeric films such as polyacrylamide; glass fibers; synthetic fibers; composites of glass and synthetic fibers; woven or non-woven glass fiber papers (coated or uncoated), plastic fibers and blends of any of these materials.

Separation media used in particular embodiments of the methods and devices provided herein are woven or non-woven glass fiber papers, coated cellulose, plastic fiber materials or blends of these materials. In other embodiments provided herein, the separation material contains long bundles of fibers or beads of any material that is inert to blood cells, does not induce severe cell lysis and creates a spacing within the range of 1-8 µm. Beads are preferably held in place or adhered together.

One or more separation media may be used in the methods and devices provided herein. In particular embodiments of the methods and devices, two separation media or more than two separation media are employed. The medium may be positioned such that fluid flow through it is normal (i.e., vertical) to the plane of the medium or within (i.e., horizontal or lateral) the plane of the medium. If two or more media are used, the media can be placed vertically, horizontally, or a combination of vertical and lateral placement can be employed. In a particular embodiment of the methods and devices provided herein, a single separation medium is positioned laterally with respect to the flow of fluid. In another embodiment of the methods and devices provided herein, two separation media are employed: (1) a first medium is placed so that fluid flow through it is vertical with respect to the plane of the medium, and (2) a second medium following, and in fluid communication with, the first medium wherein fluid flow through the second medium is lateral with respect to the plane of the medium. Typically, a fine separation and high resolution of a component of interest for use in detecting and/or quantifying the component in a fluid is conducted in a lateral flow format of a separation medium. Accordingly, use of a vertically placed separation medium in the methods and devices provided herein is generally in addition to a horizontally placed separation medium and for the purpose of providing an initial gross separation of the component of interest from other components in the fluid mixture and/or staggering the presentation of the components of the fluid mixture to the lateral separation.

b. Movement of Components of a Fluid Mixture in Separation Media

Movement of a component(s) of a fluid mixture in separation media can be effected in several ways. In one method, movement of component(s) involves internal forces or influences that are provided by the materials and/or the design of the system that includes the separation medium or media. Internal forces include, but are not limited to, capillary action, wicking, bulk flow and pressure differentials. Internal influences include, but are not limited to, diffusion, chemical or biological reactions, interparticle and particle-medium adhesion.

The material(s) of which the separation medium is composed can serve to promote the movement of a component(s) of a fluid mixture in a number of ways. For example, a porous separation medium, and, in particular, a thin, porous separation medium, provides a substrate for diffusion of the fluid mixture that contacts the medium. Porous separation media may also provide a wicking force that pulls the fluid mixture into and through the medium.

The design of the separation medium, and the system of which it is a part, can also affect movement of a component(s) of a fluid mixture. For example, a section of separation media exhibiting low capillary forces could be placed in series in fluid contact with a section of separation media having higher capillary forces. When the fluid front moves from the former to the latter media, the increased capillary forces would increase the velocity of the fluid migration, which would have an effect on the separation of the components. In another example, the separation medium can be compressed in order to minimize variability in the thickness of the medium thereby controlling the volumetric uptake of blood. Embodiments of the device provided herein in which compression of the separation medium occurs are described herein.

In alternative methods, forces external to the materials and design of the separation system are involved in effecting movement of the blood component(s) within the separation medium or media. These ancillary motive forces include, but are not limited to, pumps, gravity and pressure. Movement of blood components in a separation medium can involve internal forces and/or influences, external forces and/or influences or a combination of internal and external forces and/or influences.

c. Cessation of the Movement of Components in Separation Media

After application of a fluid sample to a separation medium, by either direct application to the medium or indirect application at a site that is in fluid communication with the separation medium, the fluid mixture is permitted to move through the separation medium due to the motive forces and/or influences acting on the fluid until flow ceases. Flow may cease for a number of reasons. For example, flow may cease because the amount of fluid applied to the medium is less than the total capacity of the medium for the fluid. In this case, flow ceases because bulk flow of the liquid due to capillary forces at the leading edge of the fluid cause the formation of a trailing edge of liquid as liquid is pulled through the medium. Capillary forces at this trailing edge oppose the capillary forces at the leading edge. Fluid movement may occur at each fluid edge due to diffusion, but no bulk flow occurs. Absent application of an external force, e.g. a pump, to the medium, the flow of fluid ceases.

Alternatively, flow in a separation medium may cease because the amount of fluid applied to the medium exceeds the total capacity of the medium for fluid. In this case, flow ceases because the medium is saturated with fluid, i.e., there is no space remaining in the medium for additional fluid. Absent some type of system for removing liquid from the saturated medium, the flow ceases and no further migration of the fluid and its components occurs in the medium.

In particular methods provided herein for separating fluid components, the amount of fluid sample applied to the separation medium is in excess of the absorptive capacity of the medium. In these methods, a particle or solid component(s) of interest moves through the medium at a slower rate than a liquid component of the fluid thereby separating from it by lagging behind the movement of the liquid front. The faster moving liquid moves ahead of the particle component(s) and fills or saturates the separation medium, at which point the motive forces responsible for movement of the component(s) cease. Thus, at that point, no further migration of the component(s) occurs.

C. Methods for Detecting and/or Quantifying Components of Fluids

1. Methods for Detecting Components of Fluids

Also provided herein are methods for detecting a component or components in a fluid. The methods are based on the separation of the component or components in a fluid using the separation methods provided herein. In separating a component within a fluid from other components, including liquid, in the fluid, the component is isolated and concentrated within a separation medium and becomes more readily detectable. Thus, through separation of the component from other components and/or liquid in a fluid mixture, it is possible to thereby detect its presence in the fluid.

In another embodiment of the methods for detecting components in a fluid, the component is an aggregate of particles or particulates. The aggregate can be formed through aggregation of the actual component particles of interest if the particle self-aggregates, or can be an aggregate of particles of interest binding to microbeads. The aggregate is indicative of the presence or absence of a secondary analyte (i.e., the secondary analyte being the unaggregated form of the "primary" analyte aggregate or component) of interest in the fluid. For ease of reference herein, an aggregate is referred to as a component of the fluid and the analyte of interest is referred to as a secondary analyte.

This method facilitates detection of particulate analytes, e.g., small molecules, that, due to their smaller size (e.g., in the 1-50 nm or less than about 100 nm range), may be difficult to separate from a fluid in a separation medium. Self aggregation of secondary analyte can be induced in a number of ways depending on the analyte. For example, aggregation can occur through protein-protein interactions, response to an enzymatic reaction, nucleic acid hybridization, small molecule binding or the condition of a separation medium or fluid, such as pH, salt levels, protein concentration. For secondary analytes that do not self aggregate, microbeads can be used to form aggregates that include the secondary analyte. Microbeads, e.g., polystyrene beads, suitable for use in these methods are available in a range of sizes, such as, for example, from about 50 nm to 15 μm. Selection of a microbead would depend on the pore size of the separation medium and the size of the particulate analyte. The microbeads can be coated with a substance that specifically binds to or interacts with a secondary analyte using techniques known in the art. The binding substance is one for which the secondary analyte has multiple binding sites. As such, the secondary analyte, when brought into contact with the coated microbeads, binds multiple microbeads thereby creating an aggregate. Binding substances for coating the microbeads include, for example, antibodies to a multi-epitope analyte, antibody fragments, aptamers, cell receptors, hybridization probes, ligands and small molecule targets. Thus, microbeads are coated with a substance that binds to a secondary analyte, they will aggregate in the presence of the analyte but will not aggregate in its absence. The microbeads are then added to a fluid sample that may or may not contain the secondary analyte of interest. The sample is applied to a separation medium in accordance with the separation methods provided herein. If the sample does not contain the secondary analyte, the microbeads will not aggregate and will separate from the fluid by migration to a particular location in the membrane. If the sample contains the secondary analyte, it will bind to the microbeads and cause aggregation of the beads which effectively forms particles of larger diameter than the unaggregated microbeads. The migration distance of the aggregate of microbeads will be different from that of the unaggregated beads, i.e., the aggregate will move more slowly in the separation medium and have a shorter migration distance. Thus, a change in migration distance of the microbeads in the presence of a sample will indicate the presence of the analyte and thereby result in detection of the secondary analyte. An example of a secondary analyte that could be detected in this manner is the iron-binding protein transferrin found in blood plasma.

Alternatively, if the secondary analyte is one for which there may not be a suitable binding partner for use in coating the microbeads, then the microbeads can be coated with a secondary analyte of interest and, optionally, a second agent that binds to a binding substance that is added to the fluid sample to promote aggregation. Examples of such secondary analytes can include small molecules, e.g., cholesterol, that do not in general have multiple antibody epitopes, receptors or ligands and nucleic acids. Microbeads coated with the secondary analyte of interest are added to a fluid sample along with a binding substance that specifically binds to multiple secondary analyte particles at once. The binding substance can be, for example, an antibody to the analyte, an aptamer designed to exhibit homo-bifunctional binding to two or more proteins or antigens, a multivalent ligand that binds the analyte, a multivalent receptor that binds the analyte or a single-stranded nucleic acid primer having multiple sequences complementary to a nucleic acid analyte, two unique oligomers, an oligomer and a DNA- or RNA-binding protein, or an oligomer and a substance that targets major or minor grooves in DNA or structural elements of RNA. The added binding substance causes aggregation of the microbeads to form particles of larger diameter than the unaggregated microbeads. The aggregates have a characteristic migration distance that is shorter than the unaggregated beads. If the secondary analyte is also present in the sample, it will compete with the secondary analyte coated on the microbeads for binding to the specific binding substance. This will result in a decrease in aggregation and a decreased number of aggregates with a corresponding increase in the number of the smaller unaggregated microbeads which have a shorter migration distance in separation media. Thus, if, after addition to a sample the migration distance of the microbeads decreases, it would be indicative of the presence of the secondary analyte in the sample.

Some fluid components can be detected upon separation and concentration in a separation medium due to an inherent property (e.g., color, fluorescence, luminescence) of the component (direct detection visually or by an instrument such as a reader). Red blood cells are an example of such a component due to the red color imparted by iron in the cells. Microbeads of different colors are also available (e.g., from Bangs Labs, Polysciences) and can, advantageously, be used for multiplexing. Other components may not be inherently detectable by visual or other manners of detection. Therefore, the methods of detecting a component(s) in a fluid as provided herein may also include a step of modifying the separated component in a way that facilitates its detection. Examples of such modifications include, but are not limited to, exposing the component to a substance that is detectable and that specifically interacts with the component such that the component thereby becomes detectable. Such substances include, but are not limited to, dyes, fluorescent labels, fluorescent microbeads, fluorescently-tagged oligonucleotides, tagged-antibodies specific to the analyte, antibodies or oligonucleotides absorbed to colored latex particle, enzyme-induced colorimetric changes or precipitations, and luminescent labels. The generation and use of detectable labels that interact specifically with a target analyte are well known in the art.

2. Methods for Quantifying Components of Fluids

Also provided herein are methods for quantifying a component or components of a fluid. The methods utilize the migration distances of components of a fluid mixture in a separation medium (or the migration areas in the medium) to determine the relative volume, also referred to as fractional or proportional volume, or concentration of a component in the fluid. In particular embodiments of the methods provided herein for quantifying fluid components, the component is a particle or solid. For example, the distance of migration (or area of migration) of red blood cells in a blood sample in a separation medium can be measured and used in determining the quantity of cells relative to the total sample.

In other embodiments of the methods for quantifying a component of a fluid, the component is an aggregate. The aggregate can be, for example, an aggregate formed by self aggregation of an analyte of interest in the fluid, or an aggregate of microbeads to which an analyte of interest in the fluid is bound or attached.

a. Migration Distances in Separation Media

As taught and described herein, the migration distance of a particle or solid component of a fluid mixture in a separation medium that has been saturated with the fluid mixture is related to, and characteristic of, the fractional volume of the component in the fluid. Thus, a fluid sample containing a particular amount of a component can be distinguished from another fluid sample containing a different amount of the same component by comparing the distances of migration of the component in a fluid-saturated separation medium for each of the two samples. Alternatively, the areas of the separation medium over which migration of the component has occurred for the two samples can be compared. Based on this association between migration distance (or migration area) and fractional volume of a component, several quantitative and semi-quantitative determinations of the relative volume of a component in a fluid can be obtained through separation of a component of a fluid sample in a separation medium that has been saturated with the fluid using the methods and devices provided herein.

For example, in one instance, the result of migration of a fluid sample containing a particular particle, aggregate or solid component through a separation medium to saturation can be compared to the result of migration of one or more other fluid samples that contain the component through an identical separation medium. The comparison can be conducted in a number of ways. For example, the separation media through which the different samples migrated can be aligned next to each other and compared with respect to the location of the component migration front (i.e., the point at which migration of the component in the medium stopped) in each medium. Differences in the locations of the component migration fronts are indicative of differing fractional volumes or differing concentrations of the components, or secondary analyte in the fluid samples. Based on this analysis, a semi-quantitative determination of fractional volume or concentration of the component, or secondary analyte in each sample can be made. Specifically, a fluid sample that resulted in a component migration front that is located more distally in the length of the separation medium than the component migration front of another fluid sample would be identified as having a greater fractional volume of the component or greater concentration of the secondary analyte than the other sample. This type of direct comparison (i.e., greater migration distances correlating with greater fractional volumes of a component or greater concentration of the secondary analyte) is possible because the separation method used in these analyses and provided herein resolves particle, aggregate or solid components of fluids in direct proportion to the fractional volume of the component or concentration of a secondary analyte. Furthermore, because the devices provided herein for fluid separation can be designed and prepared to provide for high resolution over particular ranges of fractional volumes, it is possible to distinguish even relatively small differences in fractional volumes of fluid components or concentrations of secondary analytes. For example, small differences in component fractional volumes or secondary analyte concentrations resulting in an only 100 micron change in migration distance can be detected.

Additionally, a more quantitative determination of the actual fractional volume or concentration of a particle, aggregate or solid component of a fluid can be made using the methods and devices provided herein. This can be accomplished by comparing the migration distance of a particular component to a calibration curve that correlates distances (or areas) and fractional volumes or concentrations. The process of generating a calibration curve is well known to those of skill in the art. Basically, the curve is generated using migration distances or areas of migration obtained by separating fluid samples with known fractional volumes or concentrations (i.e., standards) of a particular particle, aggregate or solid component in a saturated separation medium according to methods provided herein. The data are plotted (migration distance or area as a function of known fractional volume or concentration) and fit to a straight line using linear regression analysis. The relative component volume or concentration of secondary analyte of a fluid having an unknown component volume or concentration of secondary analyte can be interpolated from the calibration curve based on component migration distance or migration area.

In embodiments of the methods in which the component is an aggregate that contains a secondary analyte, a determination of the degree of aggregation of the analyte can provide a means of assessing and/or measuring the concentration of the secondary analyte. In embodiments in which the secondary analyte self aggregates or forms aggregates by binding or interacting with microbeads, the more aggregation that occurs, and the longer the migration distance of the aggregate, the greater the concentration of the secondary analyte in the fluid. In embodiments in which secondary analyte in the fluid competes with secondary analyte bound to microbead aggregates, the more that aggregation is reduced, i.e., the shorter the migration distance of the aggregates, the greater the concentration of the secondary analyte in the fluid.

b. Correlation of Migration Distances with Assessment Parameters

The fractional volume of a component of a fluid, or the concentration of a component of a fluid, either of which can be determined using methods and devices as provided herein based on the migration of fluid components in a separation medium, are measurements that can be used in the quantification of further aspects of a fluid and components thereof. In addition, the fractional volume of a component of a fluid and the concentration of a component, form the basis of a number of parameters having applications in medicine, including human and veterinary medicine, industry (e.g., the food industry and water treatment industries) and home testing needs.

For example, there are a number of blood parameters that are used in medical applications such as, for example, diagnosing or detecting diseases and disorders and monitoring treatment of such conditions. Some of these parameters are based on the fractional volume of cells, such as red blood cells, white blood cells and platelets, in whole blood. The methods and devices provided herein for separating blood components and determining the fractional volume of cells in blood can thus be used in determining blood parameters.

i. Hematocrit

Hematocrit (also referred to as packed cell volume or erythrocyte volume fraction) is the proportion of blood volume that is occupied by red blood cells (i.e., the percent of blood that is red blood cells). In other words, it is the ratio of the volume occupied by packed red blood cells to the volume of the whole blood. The hematocrit associated with a healthy individual (i.e., "normal" hematocrit) can be altered in some diseases or disorders such that it is lower or higher than the normal value. Examples of conditions associated with a low hematocrit include anemia and hemorrahage, whereas exemplary conditions associated with high hematocrit include polycythemia vera, dehydration, pulmonary conditions associated with hypoxia (e.g., chronic obstructive pulmonary disease or COPD), blood doping, erythropoietin use and dengue fever shock syndrome.

Provided herein is a method for determining the hematocrit of a blood sample (test sample). The method includes correlating the distance of migration of red blood cells in a separation medium that has been saturated with the test sample of blood with the migration distances of red blood cells in a separation media that had been saturated with blood having known fractional volumes of red blood cells (standards). The fractional red blood cell volume of the standard having a red blood cell migration distance that matches the migration distance of red blood cells from the test sample is the fractional red blood cell volume for the test sample.

ii. Total Hemoglobin

Hemoglobin is the iron-containing oxygen transport protein found within red blood cells. The concentration of hemoglobin in a blood sample (typically expressed in g/dl blood) is another parameter that is used in diagnosing anemia. Because there is a linear relationship between hematocrit and hemoglobin concentration, it is possible to calculate hemoglobin concentration based on hematocrit using the following conversion formula: hematocrit (%)=(0.03×hemoglobin (g/dl)+0.0083)×100. Accordingly, hematocrit determinations using the methods provided herein can be used to determine hemoglobin concentration of a blood sample.

D. Device for Measuring Parameters Associated with the Detection of an Analyte or Migration of an Analyte in a Fluid Separation Medium Provided herein is a device for separating and analyzing components (particulate components or analytes, and liquid components) in fluids. The device provided herein is constructed to permit analysis of any particulate analyte that is suspended in a known or unknown amount of fluid (cells, microorganisms, chemicals, contaminants in water, components of milk, pigments in ink, etc.). Precise measurement or metering of the fluid is not necessary for analysis with the device provided herein. The desired property of the analyte is assessed after the fluid proceeds through to saturation along a separation medium in the device (e.g., its presence or absence in the fluid, its relative or absolute amount in the fluid, its absolute or relative migration along the separation medium). The resulting assessment is then used to measure a parameter associated with the analyte.

In an exemplary embodiment, the fluid can be blood, and the device provided herein can be used to separate red blood cells (particulate component or analyte) from plasma (liquid component). The property of the analyte that is assessed is the migration of the red blood cells along the indicator strip of the device, after the device is saturated with the fluid. The extent of migration is then used to measure a blood parameter that is indicative of anemia, namely, hematocrit or total hemoglobin.

The device provided herein includes the following physical elements that can be adhered in a layered format to generate the assembled device: a proximal bottom, proximal housing, proximal cover, vertical separator, indicator housing, indicator strip and distal top portion. Without being bound by a particular mechanism or configuration, the elements thus assembled can create within the device a fluid pathway as follows: a proximal well for receiving a blood sample which is in fluid communication with a volumetric capillary reservoir for transfer of the sample to the underside of a vertical separator via a distal exit orifice, and a point of contact between the top of the vertical separator and the proximal end of the indicator strip.

a. Overall Configuration and Dimensions

The dimensions of the device provided herein can range from about 0.125 to about 0.15, 0.2, 0.3, 0.5, 0.8, 1, 1.5, 2, 2.5 or 3 inches wide and about 0.5 to 1, 2, 3, 4, 5, 6, 7, 8, 9 or 10 inches long. In one embodiment, the device is 0.787 inches wide by 3.0 inches long. In an exemplary embodiment, an assembled device is rectangular in shape with rounded proximal and distal ends.

The outer housing of an exemplary device provided herein is a rigid material. Any one of a number of rigid materials known to those of skill in the art can be used, including, but not limited to, acrylonitrile butadiene styrene (ABS), Black (CYCLOLAC® MG47-BK4500); acrylonitrile butadiene styrene (ABS), Black (LUSTRAN® 433-904000); acrylonitrile butadiene styrene (ABS), Black (POLYLAC® PA-765); acrylonitrile butadiene styrene (ABS), Black (POLYLAC® PA-746); acrylonitrile butadiene styrene (ABS), Light Grey (Platable) (LUSTRAN® PG 298-703693); acrylonitrile butadiene styrene (ABS), Natural (LUSTRAN® 433-000000); acrylonitrile butadiene styrene (ABS), Natural (POLYLAC® PA-765 (Natural)); acrylonitrile butadiene styrene (ABS), Sno White (LUSTRAN® 348-012002); acrylonitrile butadiene styrene (ABS), White (LUSTRAN® 248-SB02664900); acrylonitrile butadiene styrene (ABS), Black 30% Glass Fiber (RTP 600 605); polycarbonate/acrylonitrile-butadienestyrene (PC/ABS), Black (CYCOLOY® C1200HF-701); polycarbonate/acrylonitrile-butadiene-styrene (PC/ABS), Black (CYCOLOY® C2950-701); polycarbonate/acrylonitrile-butadiene-styrene (PC/ABS), Black (BAYBLEND® FR 110-901510); polycarbonate/acrylonitrile-butadiene-styrene (PC/ABS), Black (BAYBLEND® T85-901510); polycarbonate/acrylonitrile-butadiene-styrene (PC/ABS), Natural (BAYBLEND® FR 110-000000); polycarbonate/acrylonitrile-butadiene-styrene (PC/ABS), Natural (BAYBLEND® T65-000000); polycarbonate/acrylonitrile-butadiene-styrene (PC/ABS), Natural (CYCOLOY® C6800-111); acetal polyoxymethylene (POM), Black 10% Glass Bead (RTP 800 GB 10); acetal polyoxymethylene (POM), Black 20% Glass Bead (RTP 800 GB 20); acetal polyoxymethylene (POM) copolymer, Black (CELCON® M90 CD3068); acetal polyoxymethylene (POM) copolymer, Natural (CELCON® M90 CF2001); acetal homopolymer, Black (DELRIN® 500 CL BK601); acetal homopolymer, Black (DELRIN® 500 P BK602); acetal homopolymer, Natural (DELRIN® 500P NC010); poly(methyl methacrylate) (PMMA) i.e. acrylic, Clear (PLEXIGLAS® V052-100); engineering thermoplastic polyurethane resin (ETPU), Natural (ISOPLAST® 202EZ); high density polyethylene (HDPE), Natural (MARLEX® 9006); liquid crystal polymer (LCP), Black 30% Glass Fiber (VECTRTA® E130i); low density polyethylene (LDPE), Natural (DOW™ LDPE 722); linear low density polyethylene (LLDPE), Natural (DOWLEX™ 2517); Nylon 6 (polyamide 6), Natural 15% Glass Fiber (ZYTEL® 73G15L NC010); Nylon 6/12 (polyamide 6/12), Black 33% Glass Fiber (ZYTEL® 77G33L BK031); Nylon 66 (polyamide 66), Black (ZYTEL® 101L BKB009); Nylon 66 (polyamide 66), Black (RTP 200 UV); Nylon 66 (polyamide 66), Black (NYLON® Select N1000EHL); Nylon 66 (polyamide 66), Natural (ZYTEL® 103 HSL); Nylon 66 (polyamide 66), Natural (ULTRAMID® 1000-2); Nylon 66 (polyamide 66), Black 13% Glass Fiber (ZYTEL® 70G13 HS1L BK031); Nylon 66 (polyamide 66), Black 13% Glass Fiber (HYLON® Select N1013HL); Nylon 66 (polyamide 66), Natural 13% Glass Fiber (ZYTEL® 71G13L); Nylon 66 (polyamide 66), Natural 13% Glass Filled (ZYTEL®70G13 HS1L NC010); Nylon 66 (polyamide 66), Black 14% Glass Fiber (ZYTEL® 8018HS BKB085); Nylon 66 (polyamide 66), Black 20% Glass Fiber (RTP 200 203 FR); Nylon 66 (polyamide 66), Black 33% Glass Fiber (ZYTEL® 70G33 HS1L BK031); Nylon 66 (polyamide 66), Black 33% Glass Fiber (HYLON® Select N1033HL); Nylon 66 (polyamide 66), Natural 33% Glass Fiber (ZYTEL® 70G33 HSIL NC010); Nylon 66 (polyamide 66), Black 40% Mineral Reinforced (MINLON® 10B40 BK061); Nylon 66 (polyamide 66), Black Impact Modifier, Rubber (ZYTEL® ST-801 BK010); Nylon 66 (polyamide 66), Natural Impact Modifier, Rubber (ZYTEL® ST-801 NC010); polybutylene terephthalate (PBT), Black (VALOX® 357-BK1066); polybutylene terephthalate (PBT), Black (CRASTIN® S610 same as 600F20BK810); polybutylene terephthalate (PBT), Black (VALOX® 364-BK1066); polybutylene terephthalate (PBT), Natural (VALOX® 357-1001); polybutylene terephthalate (PBT), Black 30% Glass Fiber (VALOX® 420SEO-BK1066-BG); polybutylene terephthalate (PBT), Natural 30% Glass Fiber (VALOX® 420 SEO Nat 1001); polycarbonate (PC), Black (LEXAN® 940-701); polycarbonate (PC), Black (MAKROLON® 2405-901510); polycarbonate (PC), Clear (MAKROLON® 2458-550115); polycarbonate (PC), Clear (LEXAN® HP1-112); polycarbonate (PC), Infrared (LEXAN® 121 S-80362); polycarbonate (PC), Smoke (RTP 300 399X71833 S-94450); polycarbonate (PC), Natural 10% Glass Fiber (RTP 300 301); polycarbonate (PC), Natural 20% Glass Fiber (LEXAN® 3412R-131); polycarbonate/polybutylene-terephthalate (PC/PBT), Black (XENOY® 6620-BK1066); polyethylene terephthalate (PET), Black 30% Glass Fiber (RYNITE® 530-BK503); polyethylene terephthalate (PET), Black 35% Glass Mica Low Warp (RYNITE® 935 BK505); polyethylene terephthalate (PET), Black 45% Glass Mineral Flame Retardant (RYNITE® FR 945 BK507); polyethylene terephthalate glycol (PETG), Clear (EASTAR™ 6763); polypropylene (PP), Natural (RTP Anti-static Permastat 100); polypropylene (PP) homopolymer, Black (MAXXAM® FR PP 301BLK1284-11S); polypropylene (PP) homopolymer, Natural (PRO-FAX® 6323); polypropylene (PP) homopolymer, Natural (PRO-FAX® 6523); polyphthalamide (PPA), Natural 35% Glass Fiber (ZYTEL® HTN 51G35HSL); polyphenylene-ether/polystyrene (PPE/PS), Black (NORYL® 731-701); polyphenylene-ether/polystyrene (PPE/PS), Black (NORYL® N300X-701); polyphenylene-ether/polystyrene/polyamide (PPE/PS/Nylon), Black 10% Glass Fiber (NORYL® GTX GTX810-1710); polyphenylene sulfide (PPS), Black 40% Glass Fiber (RYTON® R-4-02); polyphenylene sulfide (PPS), Natural 40% Glass Fiber (RYTON® R-4); polyphenylsulfone (PPSU), Natural Transparent Amber (RADEL® R-5000 NT); general purpose polystyrene (GPPS), Clear (STYRON™ 666DW2); high impact polystyrene (HIPS), Natural (STYRON™ 498); polysulfone (PSU), Natural (UDEL® P-3703 NT 11); styrene butadiene (SB), Clear (K-RESIN® KR01); thermoplastic elastomer (TPE), Black (SANTOPRENE® 101-64); thermoplastic elastomer (TPE), Black (SANTOPRENE® 101-73); thermoplastic elastomer (TPE), Black (SANTOPRENE® 111-35); thermoplastic elastomer (TPE), Black (SANTOPRENE® 111-45); thermoplastic elastomer (TPE), Black (Santoprene 111-55); thermoplastic elastomer (TPE), Black (SANTOPRENE® 111-87); thermoplastic elastomer (TPE), Natural (SANTOPRENE® 211-45); thermoplastic elastomer (TPE), Natural (SANTOPRENE® 211-64); thermoplastic elastomer (TPE), Natural (SANTOPRENE® 251-70W232); thermoplastic polyurethane elastomer (polyester) (TPU-Polyester), Natural (TEXIN® 245); and thermoplastic polyurethane elastomer (polyether) (TPU-Polyether), Natural (TEXIN® 985-000000).

The outer housing forming the top of the device also can include an opening for air escape. A portion of the top of outer housing can be positioned above the narrow midsection of the indicator strip to facilitate visualization of the interface of the separated blood cell and plasma following migration through the strip. Additional portions of the top of the outer housing can include proximal and distal windows positioned above the proximal and distal wide ends of the indicator strip, which provide visual indications of successful migration of blood through the strip. The portion(s) can have relieved windows to view the indicator strip and the proximal and distal lobes. Alternatively, the portion(s) can be a transparent solid material through which the indicator strip and proximal and distal lobes can be viewed. Exemplary transparent, solid materials that can be used are known to those of skill in the art and include, but are not limited to, general purpose polystyrene (GPPS), Clear (STYRON™ 666DW2); polyethylene terephthalate glycol (PETG), Clear (EASTAR™ 6763); polycarbonate (PC), Clear (MAKROLON® 2458-550115); and poly (methyl methacrylate) (PMMA) i.e. acrylic, Clear (PLEXIGLAS® V052-100).

b. Proximal Bottom

The Proximal Bottom creates the closure for a volumetric capillary reservoir as well as provides a surface for the blood sample to be applied. The proximal bottom is a solid, thin, rigid material having an outer surface and an inner surface. Such materials are known to those of skill in the art and include, but are not limited to, styrene, propylene, acrylonitrile methylacrylate copolymer (BAREX®), polyethylene terephthalate glycol (PETG), rigid poly(chloroethanediyl) (Polyvinyl Chloride or PVC), and amorphous polyethylene terephthalate (APET). The thickness of the material can range from about 0.003 inches to about 0.005, 0.007, 0.008, 0.01, 0.015, 0.0175 or 0.020 inches. In some embodiments, the thickness is 0.010 inches. The outer surface of the proximal bottom provides the outer-facing, solid base of the device, whereas the opposite, or inner, surface provides the inner-facing bottom of the device. The inner-facing bottom serves as a bottom of a volumetric capillary reservoir and can also provide a surface for the fluid sample to be applied. In an exemplary embodiment, the fluid sample to be applied is blood. The fluid sample application area of the inner surface of the proximal bottom can be coated with materials that facilitate preservation, migration or other property of the fluid (for example, when the fluid is blood, the inner surface of the proximal bottom can be coated with heparin or other clotting inhibitor to inhibit clotting of the blood sample, and/or a buffer such as polysorbate 20 (i.e. Tween-20®) to promote migration of blood into the volumetric capillary reservoir).

c. Proximal Housing

The Proximal Housing is bonded to the Proximal Bottom. The Proximal Housing sets the volume for the capillary reservoir and directs the fluid sample to the distal exit of the volumetric capillary reservoir. The Proximal Housing also contains a thin, rigid material as described for the Proximal Bottom, and in a range of thickness as described for the Proximal Bottom. In an exemplary embodiment, rigid Polyvinyl Chloride can be used as the material, at a thickness of about 0.020 inches. The material in some embodiments is inert to the fluid, such as blood; exemplary materials include plastic, glass and metal. The material can be prepared, coated, or covered in a way to prevent the fluid, such as blood, from travelling across it and instead traveling exclusively within the strip to facilitate proper separation. Any coating known to those of skill in the art to create a hydrophobic surface, such as an adhesive, can be used. In some embodiments, the size and shape of the Proximal Housing are similar to or the same as those of the Proximal Bottom.

The Proximal Housing includes a hole in the shape of a tear drop of about 0.1, 0.2, 0.3, 0.4, 0.5, 0.55, 0.575, 0.576, 0.6, 0.7, 0.75, 0.8, 0.9 or 1.0 inch long, center to center. In one embodiment, the tear drop-shaped hole is 0.576 inch long, center to center, with the wide end of the tear drop positioned proximally compared to the position of the narrow end of the tear drop. The Proximal Housing can be adhered to the Proximal Bottom using adhesive transfer tape, glue or other adhesive known to those of skill in the art. Once adhered to the Proximal Bottom, the edges of the hole in the Proximal Housing provide the walls of a volumetric capillary reservoir and set the volume for the reservoir. The volume of the reservoir can be in a range of about 1 microliter to about 5, 10, 15, 20, 25, 30, 35, 40, 45, 50, 55, 60, 65, 70, 75, 80, 85, 90, 95 or 100 microliters or more. In some embodiments, the volume of the reservoir is from about 25 to about 30, 31, 32, 33, 34, 35, 36, 37, 38, 39 or 40 microliters.

The capillary reservoir can include any surface that permits the fluid, such as blood, to pass over it. In some embodiments, when the fluid is blood, the surface is hydrophilic, or hydrophobic with a coating that renders it hydrophilic. The capillary reservoir can also be replaced with a porous material that the blood can soak into, as long as the pore size is large enough to prevent blood cells (~1-8 µm particle size) from separating from plasma before entering the separation medium (indicator strip) (e.g., porous material of pore size of 20 um or more in diameter). In some embodiments, the capillary reservoir is not present and the fluid, such as blood, is directly applied to the strip.

The wide, circular end of the tear drop shape of the reservoir can be used to deliver the fluid to the device. The edges of the reservoir and the portion of the proximal cover that caps the volumetric capillary reservoir can be coated with substance or solutions that inhibit degradation of the fluid and/or promote migration of the fluid. In an exemplary embodiment, when the fluid is blood, the coating can be heparin and/or a buffer such as polysorbate 20 (i.e. Tween-20®) solution to inhibit clotting of the blood and to promote migration of blood into the volumetric capillary reservoir.

d. Proximal Cover

The Proximal Cover is bonded to the Proximal Housing. The Proximal Cover caps the volumetric capillary reservoir and provides the distal exit orifice. The distal exit is sized and located to promote capillary wicking into the Vertical Separator. The Proximal Cover contains a thin, rigid material known to those of skill in the art and as described in regard to the Proximal Bottom and the Proximal Housing. Such materials can include styrene, propylene, acrylonitrile methylacrylate copolymer (BAREX®), polyethylene terephthalate glycol (PETG), rigid poly(chloroethanediyl) (Polyvinyl Chloride or PVC), and amorphous polyethylene terephthalate (APET). In some embodiments, the material is rigid Polyvinyl Chloride.

The thickness of the Proximal Cover can range from about 0.003 inches to about 0.005, 0.007, 0.008, 0.01, 0.015, 0.0175 or 0.020 inches. In some embodiments, the thickness is 0.010 inches. In other embodiments, the size and shape of the proximal cover can be similar to or about the same as those of the proximal housing. The Proximal Cover contains two holes; the first hole is circular in the shape of about 0.2, 0.3, 0.4, 0.5, 0.6, 0.7, 0.8, 0.9 or 1.0 inches in diameter and is positioned proximally with respect to the second hole. In some embodiments, the second hole is smaller than the first (proximal) hole; in one embodiment, it is less than about 0.2 inches in diameter and is about 0.1, 0.125, 0.15, 0.175, 0.18 or 0.19 inches in diameter. The Proximal Cover is adhered to the Proximal Housing, using adhesive transfer tape, glue or other adhesives known to those of skill in the art such that the larger, proximal, circular hole is positioned over the wide, circular end of the tear drop shape of the reservoir formed by the Proximal Housing. In some embodiments, the portion of the Proximal Cover that caps the volumetric capillary reservoir and edges of the reservoir can be coated with substances or solutions that inhibit degradation of the fluid and/or promote migration of the fluid into the volumetric capillary reservoir. In an exemplary embodiment, the fluid is blood and the coating can be heparin and/or a buffer such as polysorbate 20 (i.e. Tween-20®) solution to inhibit clotting of the blood and promote migration of blood into the volumetric capillary reservoir.

Once adhered, the Proximal Cover caps the volumetric capillary reservoir, leaving a circular opening for the blood sample delivery reservoir. The smaller, distal circular hole in the Proximal Cover provides the distal exit orifice of the volumetric capillary reservoir. The distal exit orifice is sized and located to promote capillary wicking of blood into the vertical separator.

e. Vertical Separator

The Vertical Separator and the Indicator Strip in combination provide the portion of the device that separates and resolves components of a fluid, after the device is saturated with the fluid. The Vertical Separator is positioned and adhered over the distal exit orifice. The distal orifice controls blood flow so that blood can only enter the indicator housing via capillary action of the test strip and is therefore unable to flow around and avoid being properly resolved within the test strip. Blood separation initially occurs through the vertical glass filter. The vertical separation results in effective separation of a relatively large volume of blood from plasma over a short distance. In doing so, the vertical flow decreases the cell mass enough so that the lateral flow portion can resolve the ratio of cells to plasma. Blood migration through a vertical separation component has some inherent variability. The wide, proximal end of the lateral Indicator Strip mitigates uneven flow of blood through the paper, allowing the blood front along the distal face of the Vertical Separator to equalize.

The Vertical Separator can be a glass fiber filter or any material that is the proper density (e.g., at about a 2-3 um pore size) that does not degrade the analyte and/or other fluid components (e.g., if the analyte is a cell, the material should not or should minimally effect cell lysis). Exemplary materials include glass, paper made from coated cellulose, cotton and synthetic fibers, or blends of various fiber materials) known to those of skill in the art. Glass is common because it induces particularly minimal cell lysis.

The Vertical Separator, in some embodiments, is of a semi-circular (crescent) shape that can be used to make the distance from any point on the distal edge of the vertical pad and the proximal edge of the resolving region of the indicator strip consistent. This promotes the fluid front to converge at the resolving region of the indicator strip. In other embodiments, the shape of the filter suitable for this purpose can include, but is not limited to, half circles, rectangles, triangles and other geometric shapes known to those of skill in the art. In general, better separation is effected with wider rather than longer Vertical Separators.

The Vertical Separator is situated and adhered to the proximal cover, directly above the distal exit orifice, using adhesive transfer tape, glue or other adhesive known to those of skill in the art. The Vertical Separator is positioned perpendicular to the plane of the housing. The distal orifice controls fluid flow so that fluid can only enter the Indicator Housing via capillary action of the Indicator Strip and is therefore unable to flow around and avoid being properly resolved within the Indicator Strip. The fluid sample is drawn into the Vertical Pad and Indicator Strip by capillary forces that occur between the liquid and the dense fibers of the Vertical Separator.

Fluid separation initially occurs through the vertical glass filter. The vertical separation results in effective separation of the components of a relatively large volume of fluid (such as the plasma and red blood cells of the fluid, blood) over a short distance. In doing so, the vertical flow decreases the analyte (e.g., red blood cell) mass enough so that the lateral flow portion can resolve the ratio of analyte (red blood cells) to the liquid component (plasma). The wide, proximal end of the lateral Indicator Strip mitigates uneven flow of fluid through the paper, allowing the fluid front along the distal face of the Vertical Separator to equalize.

In general, the vertical and lateral flow separators (Vertical Separator; Indicator Strip) can be any material that has a pore size, fiber density, or bead density capable of separating particulate analytes (or particulate aggregates of soluble analytes) from the liquid components of a fluid. For example, in measuring hematocrit based on the migration of red blood cells separated from plasma, the pore size can be ~1-8 um in diameter; in some embodiments it is between about 2 to about 3 um in diameter. (Note that red blood cells have an average diameter of 7-8 um, but can deform dramatically). The pore size can empirically be determined by the ability to effect differential migration of the particulate analyte of interest relative to the other analytes and/or liquid components in the fluid. Suitable separation materials include papers: woven or non-woven glass fiber papers (coated or uncoated), coated cellulose, plastic fiber materials, synthetic materials or a blend of two or more thereof, long bundles of fibers will work, and beads that are made of a material inert to the particulate analyte of interest in the fluid and/or the fluid. The beads can be held in place or adhered together on the separator.

In some embodiments, the separator need not be a distinct material; rather, the housing can be etched to create channels through which the fluid travels. Without being bound by any theory, capillary forces within the etched channels could induce migration of the fluid, such as blood, within the channels. The size of the channels can be empirically designed based on the differential separation to be effected between the particulate analyte of interest and the remaining components of the fluid. In some embodiments, the surfaces of the channels can be prepared, coated, or covered in a way to prevent the fluid, such as blood, from travelling across it and instead traveling exclusively within the strip to facilitate proper separation. Any coating known to those of skill in the art to create a hydrophobic surface, such as an adhesive, can be used.

f. Indicator Housing

The Indicator Housing is bonded to the Proximal Cover and provides a minimal internal volume around the separation components. This prevents humidity and other environmental variables from affecting fluid migration characteristics in the device. The Indicator Housing is made from a thin rigid material known to those of skill in the art and including, but not limited to, styrene, propylene, acrylonitrile methylacrylate copolymer (BAREX®), polyethylene terephthalate glycol (PETG), rigid poly(chloroethanediyl) (Polyvinyl Chloride or PVC), and amorphous polyethylene terephthalate (APET). In some embodiments, rigid Polyvinyl Chloride is used. The thickness of the material can range from about 0.038 inches to about 0.042 inches; in some embodiments, the thickness is 0.040 inches. The size and shape of the Indicator Housing are similar to or the same as those of the Proximal Cover.

The Indicator Housing has two holes; one hole is circular in the shape of about 0.1, 0.2, 0.3, 0.4, 0.5, 0.6, 0.7, 0.8 0.9 or 1.0 inches in diameter and is positioned proximally with respect to the second hole. The second hole has a shape similar or identical to the shape of the Indicator Strip (e.g., dumbbell or other shape with wider ends flanking a narrow midsection). In an exemplary embodiment, the Indicator Housing is in the shape of a dumbbell having a narrow rectangular midsection about 0.1, 0.15, 0.2, 0.25, 0.3, 0.35, 0.4, 0.45 or 0.5 inches wide and 0.5, 0.55, 0.6, 0.65, 0.7, 0.75, 0.88, 0.85, 0.9, 0.95 or 1.0 inches long and about 0.5 inch to 1.0 inch diameter wide circular ends.

The Indicator Housing is adhered to the Proximal Cover (using adhesive transfer tape, glue or other adhesives known to those of skill in the art) such that the circular proximal hole in the Housing is positioned directly above the circular proximal hole in the Proximal Cover. In positioning the Indicator Housing in this way, the Vertical Separator is located in, and perpendicular to the plane of, the proximal wide circular end of the second (dumbbell or other shape with wide ends flanking a narrow midsection) hole. The Indicator Housing provides a minimal internal volume around the separation components. This prevents humidity and other environmental variables from affecting fluid migration characteristics in the device.

Alternate Embodiment of the Indicator Housing

In one embodiment, the Indicator housing can be designed to compress the indicator strip between two layers of adhesive (adhesive transfer tape such 3M's 467 MP 2.3 mils adhesive transfer tape, glue or other adhesive known to those of skill in the art)-coated rigid material. Types of rigid materials include, but are not limited to, styrene, propylene, acrylonitrile methylacrylate copolymer (BAREX®), polyethylene terephthalate glycol (PETG), rigid poly(chloroethanediyl) (Polyvinyl Chloride or PVC), and amorphous polyethylene terephthalate (APET). In one embodiment, the material is Rigid Poly Vinyl Chloride. The thickness can range from about 0.1 to about 0.11, 0.12, 0.13, 0.14, 0.15, 0.16, 0.17, 0.18, 0.19, 0.20, 0.21, 0.22, 0.23, 0.24 or 0.25 inches. In one embodiment, the thickness is from about 0.019 inches to about 0.021 inches. In another embodiment, the material is Rigid Poly Vinyl Chloride and the thickness is 0.020 inches. The compression can minimize variability in the thickness of the Indicator Strip material, thereby controlling the volumetric uptake of the fluid, such as blood. The size and shape of the Indicator Housing are the same as those of the Proximal Cover.

In one embodiment, there are two openings in the Indicator Housing; the first is a circular opening of about 0.5 inches in diameter. The second opening is positioned distally in respect to the first opening, and is in the shape of a dumbbell having a narrow rectangular midsection 0.25 inches wide and 0.75 inches long, with 0.5 inch diameter wide circular ends. In this manifestation, the Indicator Housing with the dumbbell-shaped opening is constrained to a thickness equal to or slightly less than the nominal thickness of the indicator strip, thereby compressing the indicator strip to a defined thickness. In one embodiment, this thickness is about 0.012 inches. The proximal end of the dumbbell opens downwardly towards the proximal hole to provide a continuous space for the Vertical Separator while maintaining face to face contact between the Vertical Separator and the Indicator Strip. This vertical shaft descending down from the proximal end of the dumbbell shaped opening is a half circle to full circle in shape, having a shared proximal surface from the dumbbell above. In one embodiment, this opening is slightly larger than a half moon at 0.35 inches long. Similar to other manifestations, the Indicator Housing is adhered using 3M's 467 MP 2.3 mils or other adhesive transfer tape, glue or other adhesive known to those of skill in the art to the Proximal Cover such that the circular proximal hole in the cover is positioned directly above the circular proximal hole in the Indicator Housing. The Indicator Housing can also serve to provide a minimal internal air space around the separation components, thereby minimizing the effects of humidity and other environmental variables on the blood migration characteristics in the device.

g. Indicator Strip

The Indicator Strip is adhered to the bottom of the Distal Top. The Distal Top is bonded to the Indicator Housing creating the sealed internal volume. Fluid separation along the Indicator Strip provides resolution, based on the analyte (e.g., red blood cells as an indicator of blood hematocrit) that can be visibly measured. The distal pad of the Indicator Strip provides a sink for excess liquid component (e.g., plasma when the fluid is blood) so that the liquid-analyte interface stabilizes along the Indicator Strip.

In some embodiments, the fluid that is separated and analyzed on the Indicator Strip is blood. Resolution of blood from plasma requires a relatively large volume of separated blood through a narrow, low capacity area. However, rapid resolution of plasma from blood enhances the overall resolution based on hematocrit. Blood migration through a narrow, low capacity area is relatively slow compared with wider, high capacity components. The dumbbell or other shape of the Indicator Strip having wide ends flanking a narrow midsection of the strip, combined with the Vertical Separator, allows a large volume of blood or other fluid to initially be resolved rapidly over a short distance, then pass through the low capacity strip before again filling a larger capacity distal sink.

The Indicator Strip is made of a thin glass-fiber lateral fluid separation material. In one embodiment, the material is MF1 from Whatman, which is a polyvinyl alcohol-bound glass fiber filter that removes particles greater than 2 μm. As with the Vertical Separator, any material that is the proper density (e.g., about a 2-3 um pore size) that does not damage the analyte (e.g., cell lysis) can be used. Such materials include, but are not limited to, paper made from coated cellulose, cotton and synthetic fibers or blends of various fiber materials known to those of skill in the art. In some embodiments, the material can be further coated with substances, such as polyvinyl alcohol, to further reduce cell lysis.

The shape of the Indicator Strip is designed to control and calibrate the range of analyte migration that can be read by the device, based on the parameter that is to be measured after the device is saturated with fluid. In some embodiments, the Indicator Strip is shaped like a dumbbell having a narrow rectangular midsection and wider circular ends. The shape of the Indicator Strip follows the shape of the second hole of the Indicator Housing.

The overall size of the Strip is slightly smaller than that of the second hole of the Indicator Housing. In some embodiments, the second hole is about 0.5 inches in diameter. The Indicator Strip is adhered (using adhesive transfer tape, glue or other materials known to those of skill in the art) to the bottom surface of the Distal Top, which, as described herein, also forms the top of the device with its outer, top surface. The Distal Top, with the Indicator Strip adhered to its bottom surface, is adhered to the Indicator Housing (using adhesive transfer tape or other materials known to those of skill in the art) such that the Indicator Strip is positioned within the second (dumbbell or other shaped) hole of the Indicator Housing, thereby creating a sealed internal volume housing the Indicator Strip. The Indicator Strip thus is contained in a space wherein the bottom, or floor, of the space provided by the Proximal Cover serves as a base for the Strip, the dumbbell or other-shaped second hole in the Indicator Housing provides the walls of the space around the Strip and the bottom surface of the Distal Top provides the roof of the space. The most proximal semicircular half (in the case of a dumbbell shape) of the proximal wide end of the Indicator Strip is situated above and in contact with the top of the Vertical Separator, which was adhered on to the Proximal Cover.

In some embodiments, a liquid-soluble dye, such as dry bromophenol blue (BPB), can be solubilized (e.g., in water or 95% ethanol) and applied onto the center of the distal pad and allowed to dry for 5 minutes. A color change in the dye (in the presence of the liquid component of the fluid) can be used as an indicator that the liquid component of the fluid (e.g., plasma, when the fluid is blood) has successfully migrated to the distal pad of the Indicator Strip, and the desired property of the migrated analyte in the central portion of the Indicator Strip can then be assessed. In another embodiment, the dye can be applied upstream from the quality indicator window so that it is not visible through the window. When the plasma is at or approaches the distal end of the Indicator Strip, the dye dissolves in the plasma and flows into the portion of the Strip visible through the window.

In an exemplary embodiment, the fluid is blood, the liquid component of the blood is plasma, and the dye is BPB. BPB is yellowish in color at low pH (below 3-4 pH), before encountering plasma. When brought to a high pH (above pH 4.6), which is what happens when exposed to plasma, the color changes to dark blue/purple, indicating that the test is complete and ready for analysis.

h. Distal Top

The Distal Top is printed with graphics indicating the function of the device. The graphics represent the range of measurement of a parameter of interest associated with an analyte that has migrated in the Indicator Strip. In exemplary embodiments, the graphics represent blood hematocrit or total hemoglobin. The range is determined based on the calibration of the device, which is described below.

The Distal Top is made of a thin rigid, transparent material such as, but not limited to, styrene, propylene, acrylonitrile methylacrylate copolymer (BAREX®), polyethylene terephthalate glycol (PETG), rigid poly(chloroethanediyl) (Polyvinyl Chloride or PVC), and amorphous polyethylene terephthalate (APET) The thickness of the material can range from about 0.003 inches to about 0.005, 0.007, 0.008, 0.01, 0.015, 0.0175 or 0.020 inches; in one embodiment the thickness is 0.010 inches. The Distal Top also includes an air escape opening of about 0.005, 0.01, 0.015, 0.02, 0.025, 0.03, 0.035, 0.04, 0.045 or 0.05 inches in diameter at the distal end of the dumbbell or other shaped Indicator Housing, allowing displaced air to escape as blood is drawn into the device. In one embodiment, the diameter of the air escape opening is about 0.020 inches in diameter.

One surface of the Distal Top forms the top of the device facing the exterior. The Indicator Strip is adhered (using adhesive transfer tape or other adhesives known to those of skill in the art) to the opposite, or bottom, surface of the Distal Top such that the narrow rectangular portion of the Indicator Strip aligned with the narrow rectangular transparent portion of the distal top and the proximal and distal windows aligned with the proximal and distal wide ends of the Indicator Strip, respectively. The windows facilitate visual observation of the presence of sufficient blood sample reaching the proximal end of the indicator strip and of successful migration of plasma through the strip to the point of saturation. The thus-formed Distal Top/Indicator Strip element was adhered (using adhesive transfer tape or other adhesives known to those of skill in the art) to the top surface of the Indicator House such that the Indicator Strip was positioned within the second (dumbbell or other-shaped) hole of the Indicator Housing, thereby creating a sealed internal volume housing the indicator strip.

i. Calibration of the Device

The device provided herein can be adjusted to a predetermined resolution or separation of the particulate analyte of interest, depending on the range of values of the associated parameter that is to be measured or assessed. In some embodiments, the device can be calibrated empirically by testing a range of control samples containing a known amount of the particulate analyte of interest or a known degree of aggregation of a particulate or soluble analyte of interest (the aggregation resulting in particle formation of the soluble analyte). For example, to measure hematocrit or hemoglobin concentration in blood, blood samples corresponding to a range of known hematocrit or hemoglobin concentration values were run through the separation medium (e.g., Indicator Strip of the device) on devices tested in parallel and the red blood cell migration distances were compared to hematocrit or hemoglobin concentration values generated on the Hemocue device or by spun hematocrit method. A linear regression of migration distance vs. hematocrit or hemoglobin concentration was plotted based on the comparison, and the device was marked with hematocrit or hemoglobin concentration values accordingly.

In other embodiments, the device can be calibrated by a separation efficiency factor R that is determined based on a number of parameters of the separation medium (e.g., Indicator Strip of the device) including the volume of liquid per unit saturated area, the shape, the length, the width and the area of the separation medium. In an exemplary embodiment, the device provided herein can be calibrated according to a desired predetermined range of hematocrit or hemoglobin concentration values to be measured using the device.

Calibration of the Device to a Predetermined Range of Hematocrit or Hemoglobin Concentration Values In general, the "separation efficiency", denoted by R, is a constant the defines the resolution properties of a porous material. In other words, although different porous materials will have different values of R, changing the size or shape of the porous components does not affect R.

With respect to blood and the determination of hematocrit or hemoglobin concentration, the Separation Efficiency R can be defined as the volume fraction of plasma separated by the porous medium, divided by the volume fraction of plasma in the original sample of whole blood. For example, a sample of blood having a hematocrit of 40% is introduced at one end of a 10 cm strip of filter paper, and migrates to the other end of the strip by capillary action until the strip is saturated. Because the red blood cells migrate slower than the plasma, a front develops, so that at saturation, the red blood cells have only migrated 6.2 cm down the strip, with the remaining 3.8 cm of the strip containing only plasma. The volume fraction of the separated plasma is therefore 3.8 cm/10 cm=0.38. The volume fraction of the plasma in the original sample is (1−40% hematocrit)=0.6. Therefore R=0.38/0.6=0.63.

In equation form (Equation 1):

$$R = \frac{\text{Volume fraction separated plasma}}{\text{Volume fraction plasma in whole blood}} \quad [1]$$
$$= \frac{(\text{Volume separated plasma})/(\text{Volume sample})}{1-H}$$

where H is the hematocrit of the sample. For the purposes described here, the volume of the sample is the volume of blood actually absorbed by the porous media. It should be noted that the definition represented by Equation 1 for the volume fraction of plasma in whole blood, one minus the hematocrit (1−H), does not consider the small amount of plasma in the interstitial space of even the most densely packed cells, nor the volume occupied by the white cells found in their own layer between the red blood cells and plasma (the buffy coat), which can segregate with the red blood cells during separation by filtration. Nonetheless, Equation 1 has proven useful in the development of a method for calibrating the device provided herein.

Rearranging the Equation 1 to solve for hematocrit gives Equation 2 below:

$$H = 1 - \frac{\text{Volume separated plasma}}{R(\text{Volume sample})}. \quad [2]$$

Where "Volume sample" in Equation 2 is the total liquid volume in the saturated porous media. "Volume separated plasma" is the liquid volume in that portion of the porous media which is saturated only with plasma.

Dimensions of area can be used when designing shapes using filter paper as the porous media. The volume of liquid per unit of saturated area is determined experimentally for each different type of filter paper, and is denoted by "ω". This technique is generally more accurate than calculating the liquid volume from the specified thickness and porosity of the filter paper (often provided by the manufacturer) since these papers usually swell when wetted, changing both the thickness and the porosity.

The basic shape (dumbbell or barbell) for the filter paper in one embodiment of the device is shown below. This barbell shape can be described as two approximately circular lobes separated by a long rectangular indicator region. The blood enters at the far end of one of the lobes, called the "proximal lobe" via the crescent-shaped vertical separator, which sits below the proximal lobe, with its longer curved edge aligned with the far edge of the proximal lobe. The proximal lobe has been shaped so that the path lengths of the blood flowing from any part of the vertical separator to the indicator region will be approximately equal. This design helps ensure a sharp interface between the red blood cells and the plasma. The design goal is to determine an overall shape so that this interface falls within the indicator region if the hematocrit of the blood falls within a specified range. Migration of the blood ceases once the lobe at the far end from the blood application, or "distal lobe," has been saturated.

Figure 6:
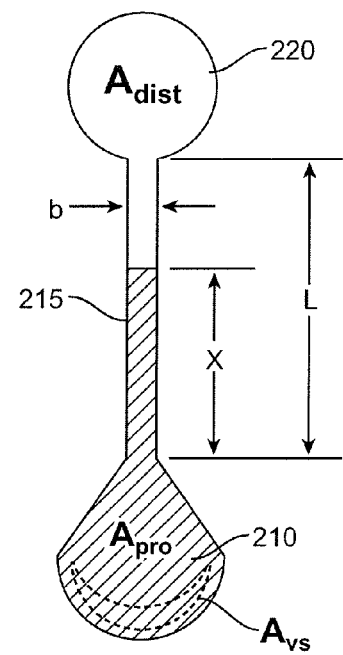
FIG. 6 shows a schematic top view of the shape of the component of FIG. 5.

As shown in FIG. 6, $A_{vs}$ is the area of the vertical separator, $A_{prox}$ is the area of the proximal lobe, $A_{dist}$ is the area of the distal lobe, and b and L are the width and length respectively of the indicator region, so that the area is b L. x is the distance from the tip of the proximal lobe to the interface between the red blood cells and plasma. In order to calculate the relevant fluid volumes, the areas are multiplied by the liquid volumes per unit area, either $\omega_{strip}$ for the filter paper, or $\omega_{vs}$ for the vertical separator.

Equation 2 therefore becomes Equation 3 below:

$$H = 1 - \frac{(L-x)b\omega_{strip} + A_{dist}\omega_{strip}}{R[[A]_{vs}\omega_{vs} + (A_{prox} + Lb + A_{dist})\omega_{strip}]} \quad [3]$$

$$= 1 - \frac{(L-x)b + A_{dist}}{R[[A]_{vsAdj} + A_{strip}]},$$

where the total area of the filter paper (excepting the vertical separator) $A_{strip}=A_{prox}+L\ b+A_{dist}$ and the adjusted area of the vertical separator $A_{vsAdj}=A_{vs}(\omega_{vs}/\omega_{strip})$. The range of the device is the hematocrit range in which the red blood cell front is located on the indicator region, that is, from x=0 to x=L. Therefore, from Equation 3 we get Equations 4a and 4b as follows:

$$H_{min} = 1 - \frac{Lb + A_{dist}}{R[[A]_{vsAdj} + A_{strip}]} \quad [4a]$$

$$H_{max} = 1 - \frac{A_{dist}}{R[[A]_{vsAdj} + A_{strip}]}. \quad [4b]$$

We define the resolution of the device as the change in the position of the red blood cell front divided by the corresponding change in hematocrit. It is desired that this be as large of possible so that differences in hematocrit are more easily resolved. Rearranging Equation 3 to solve for x gives Equations 5 and 6 below:

$$x = L - \frac{R(1-H)[[A]_{vsAdj} + A_{strip}] - A_{dist}}{b}; \quad [5]$$

so that:

$$\text{resolution} = \frac{dx}{dH} = \frac{R[[A]_{vsAdj} + A_{strip}]}{b}. \quad [6]$$

Greater resolution is thus achieved with larger areas and smaller widths b of the indicator region. Larger areas also lead to larger sample volumes, which generally are not desirable (Equation 7):

$$\text{sample volume} = A_{vs}\omega_{vs} + A_{strip}\omega_{strip}. \quad [7]$$

The above analysis can readily be modified according to the shape of the indicator region, including more complex shapes such as, for example, a non-rectangular indicator region, for instance a region which changed its width between the proximal lobe and the distal lobe, and a variation of the separation efficiency R with hematocrit H. Modifications can be made to Equation 2, and the corresponding succeeding equations derived, using standard geometrical and algebraic methods known to those of skill in the art.

j. Relationship Between Hematocrit and Hemoglobin Concentration

In general, there is a linear relationship between hematocrit and hemoglobin concentration. Empirically, the values are interchangeable by dividing % Hematocrit by 3, to approximately arrive at Hemoglobin in g/dL. For example, 24% HCT (Hematocrit)~=8 g/dL Hgb (Hemoglobin). The conversion equation is as follows:

HCT (%)=(0.03×Hgb (g/dL)+0.0083)×100

Thus, the method and device provided herein can be used to measure hematocrit or hemoglobin concentration by measuring the migration of red blood cells in the separation medium.

k. Exemplary Device

An exemplary device and method for visualizing hematocrit in a blood sample are described. The method includes a process by which administered blood is exposed to heparin to prevent clotting, then separated through a vertical separation paper, and focused onto a graduated indicator strip that correlates migration distance of the separated blood cells with hematocrit. Blood need not be metered prior to migration onto the blood separation paper. The blood separation paper achieves saturation and this arrests any further migration of the blood along the separation strip. In an embodiment, migration of the blood takes less than 15 minutes and can be read once saturation of the strip has been reached. The device includes an indicator along the test strip that indicates to the user that the blood has migrated the entire distance of the test strip thereby providing an indication that the test was successful. In addition, the device embodies an indicator along another portion of the test strip to indicate to the user when sufficient blood has been added.

FIG. 1 shows a top view of an exemplary embodiment of the device 105. The device includes a well 110 that is configured to receive a sample of blood. One or more indicator windows are located on the device for providing relevant information to the user. For example, a first indicator window 115 provides an indication as to when a sufficient amount of blood has been applied to the device. A second indicator window 120 provides an indication as to whether the device has ran correctly. The indicator windows can be configured to display a predetermined color (such as red or blue) or other indication to represent that a certain criteria has been satisfied. A graduated scale 125 is located on the front of the device to indicate the value of hematocrit/hemoglobin. The illustrated embodiment of the device generally has an elongated shape (from a proximal end 130 to a distal end 135) that is configured to be held by a user. It should be appreciated that the shape and size of the device may vary.

One or more labels may be provided on the device to provide any of a variety of information to the user. For example, a label 110 adjacent the well 110 includes language such as "Apply Blood Here" to indicate to the user that blood should be applied to the well 110. Any of a wide variety of other labels can be provided on the device.

FIG. 2 shows a top view of the device 105 with a top cover removed. FIG. 3 shows a side, cross-sectional view of the device 105. The well 110 (which is configured to receive blood) forms an opening in the top of the device and extends downwardly toward the bottom of the device. As shown in FIG. 3, the bottom end of the well 110 communicates with a capillary reservoir 205 that extends from the well 110 toward the distal end 135 of the device. As shown in FIG. 2, the capillary reservoir tapers in size moving from the well in a distal direction.

The capillary reservoir 205 communicates with a vertical separator 210 that provides a pathway for fluid to flow from the capillary reservoir 205 toward an elongated indicator strip 215 that is positioned at least partially above the capillary reservoir. The indicator strip 215 may be lateral separation paper. In an embodiment, the indicator strip 215 is made from a thin glass-fiber lateral blood separation material. The indicator strip 215 extends distally along the length of the device and terminates at an excess volume reservoir 220 that is configured to receive and collect excess volume of fluid, as described more fully below. It should be appreciated that FIG. 3 is not drawn to scale. In an embodiment, the indicator strip is dye-free. The depth and relative sizes of various components may be exaggerated for clarity of illustration.

Figure 4:
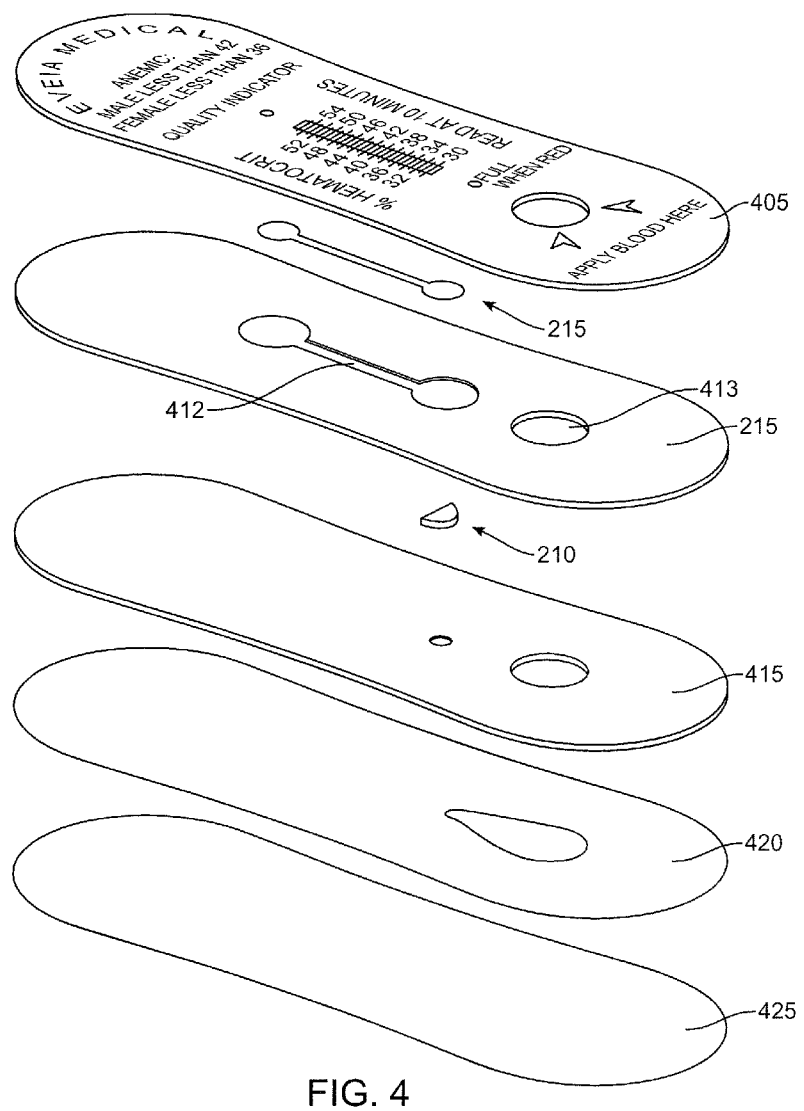
FIG. 4 shows an exploded view of an exemplary set of layered components that form the device.

The device 105 may be formed of various components that are assembled to collectively form the device. FIG. 4 shows an exploded view of an exemplary set of layered components that form the device 105. It should be appreciated that the configuration of the components can vary and is not limited to what is shown in FIG. 4. A top cover 405 forms a top layer of the device. The indicator strip 215 is positioned immediately below and adjacent the top cover 405 such that the indicator strip 215 is adhered to the underside of the top cover 405. A middle layer 410 is positioned below the top cover 405 and includes a cut-out 412 that comprises an indicator housing around the separator components of the device. The vertical separator 210 is sized and shaped to be positioned at least partially within the cut-out 412. The vertical separator 210 is adhered to the top of a layer 415 such that it extends upwardly through the cut-out 412 and communicates with the indicator strip 215. An additional middle layer 420 is positioned below the layer 415 and above a bottom layer 425, which forms a base of the device. The layers may include various additional cut-outs that align with one another to form reservoirs and/or passageways of the device 105, such as, for example, the capillary reservoir 205, the well 110, and the excess volume reservoir 220.

Figure 5:
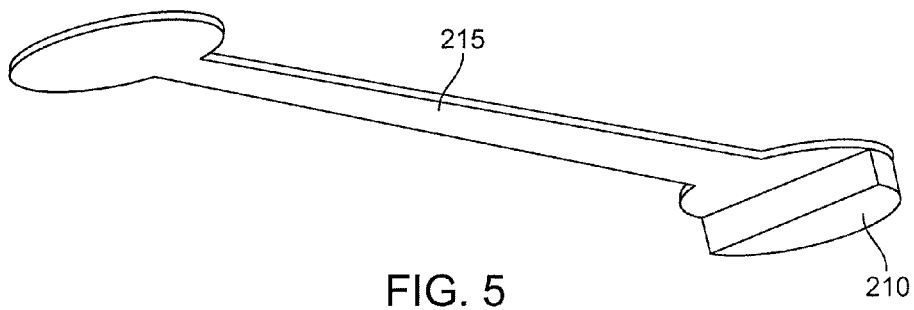
FIG. 5 shows an exemplary component that enables blood separation in the device.

FIG. 5 shows an exemplary component that enables blood separation in the device 105. The component has a shape that is configured to resolve variations in hematocrit over a measurable distance. FIG. 6 shows a schematic top view of the shape of the component. The component has a pair of widened or enlarged ends for blood collection and a narrow mid-section such that the component has a general "dumbbell" shape. In other words, the component has two approximately circular or rounded lobes on opposite ends separated by a long rectangular indicator region.

With reference to FIGS. 5 and 6, the vertical separator 210 is positioned at one end of the component. In an embodiment, the vertical separator is crescent-shaped. The capillary reservoir forms a pathway between the vertical separator 210 and a first end (proximal end) of the indicator strip 215. The opposite, second end (distal end) of the indicator strip 215 communicates with the excess volume reservoir 220.

An exemplary method of using the device is now described. A sample of blood is deposited into the well 110 via the opening on the top of the device. The blood sample application area may be coated with heparin to inhibit blood clotting and a mild solution (such as Tween-20® solution) to promote migration of blood into the volumetric capillary reservoir 205. Blood passes through the well (such as via adhesion properties) into the capillary reservoir 205, as represented by arrows X and Y in FIG. 3. The edges of the capillary reservoir 205 (or any other portion of the device) may be coated with heparin to inhibit blood clotting and a mild solution (such as Tween-20®) solution to promote migration of blood to the distal exit of the volumetric capillary reservoir.

From the capillary reservoir 205, blood flows to the underside of the vertical separator 210, where the blood is pulled upwardly (such as via capillary and bulk-flow properties) toward and onto the indicator strip 215. The vertical separator 210 may be positioned and adhered over a distal exit orifice that controls blood flow so that blood can only enter the indicator region of the device via capillary action of the indicator strip and is therefore unable to flow around and avoid being properly resolved within the indicator strip. Blood separation initially occurs through a vertical glass filter of the vertical separator 210. The vertical separation results in effective separation of a relatively large volume of blood from plasma over a short distance. In doing so, the vertical flow decreases the cell mass enough so that the lateral flow portion can resolve the ratio of cells to plasma. Blood migration through a vertical separation component has some inherent variability. The wide, proximal end of the lateral indicator strip 215 mitigates uneven flow of blood through the paper, allowing the blood front along the distal face of the vertical separator 210 to equalize.

The blood migrates in a proximal-to-distal direction down the indicator strip 215, as represented by arrow Z in FIG. 3. Blood separation along the indicator strip provides resolution, based on hematocrit, that can be visibly measured. As mentioned, the top of the device has a graduated scale 125 that indicates percent hematocrit based on blood migration along this narrow section of the indicator strip. The distal section of the indicator strip 215 provides a sink for excess plasma so that the blood plasma interface stabilizes along the indicator strip. Resolution of blood from plasma requires a relatively large volume of separated blood through a narrow, low capacity area. However, rapid resolution of plasma from blood enhances the overall resolution based on hematocrit. Blood migration through a narrow, low capacity area is relatively slow compared with wider, high capacity components. Thus, the "dumbbell" shape of the indicator strip 215 combined with the vertical separator 210 allows a large volume of blood to initially be resolved rapidly over a short distance, then pass through the low capacity strip before again filling a larger capacity distal sink. The excess volume reservoir 220 collects excess volume until saturation of the paper is reached and no further blood migration can occur.

Dry bromophenol blue may be present on the distal region of the indicator strip. The powdered dye becomes visibly blue upon contact with liquids including plasma. The blue color provides an easy indicator that plasma has successfully migrated to the distal pad of the indicator strip, indicating a successful run. In an embodiment, the blue color can be observed through the window 120 (FIG. 1). The device may includes an air escape opening allowing displaced air to escape as blood is drawn into the device.

Figures 7, 8:
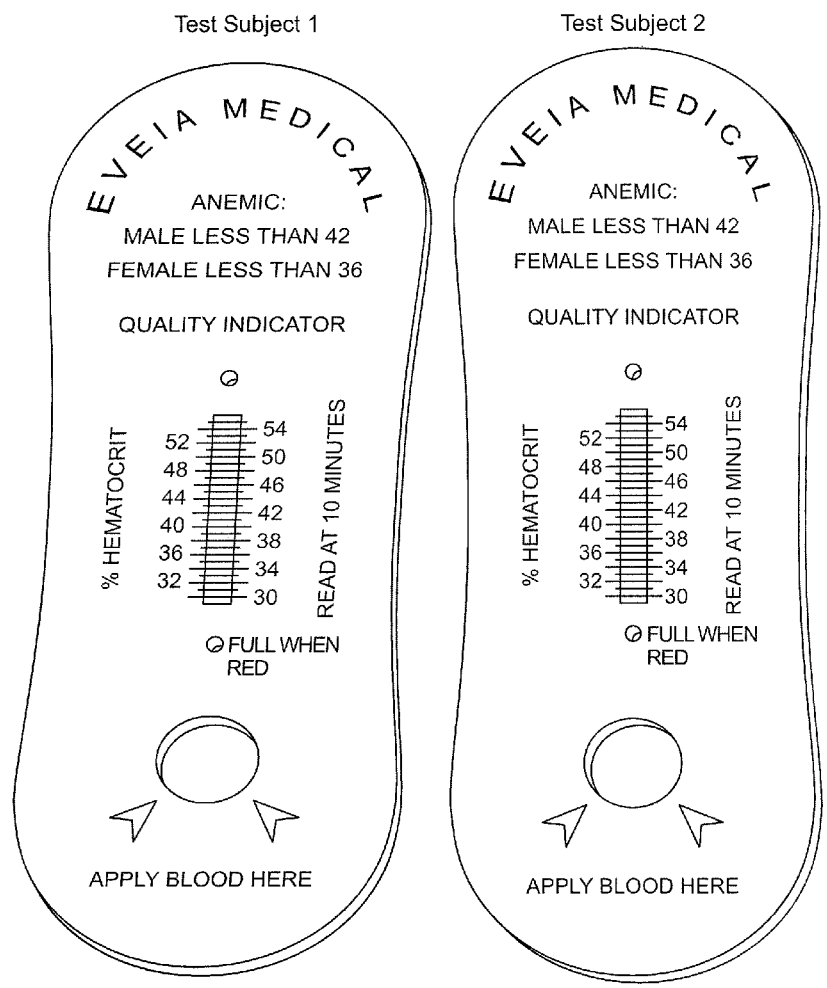
FIGS. 7 and 8 show examples of assembled devices post-delivery of capillary blood.

FIGS. 7 and 8 show examples of assembled devices post-delivery of capillary blood. The indicator windows on each device properly turned red when enough blood had been administered. As demonstrated on the device shown in FIG. 7, the indicator window that the shows the device worked properly turned a predetermined color (such as blue). The indicator strip measured the hematocrit at 52% for the device of FIG. 7, which is consistent with definitive laboratory hematocrit tests for this subject's blood and 50% for the device of FIG. 8. Tests performed using lower hematocrit samples showed less migration of the red blood cell front as expected.

In another embodiment, the housing of the device is configured such that the indicator strip 215 is compressed when positioned inside the housing. In this regard, the indicator strip 215 may be positioned between a pair of layers, such as adhesive-coated rigid material, that compress the indicator strip 215. In an embodiment, the adhesive layers are 467 MP 2.3 mils adhesive transfer tape (such as manufactured by 3M) and the rigid material is a material such as Styrene, propylene, Barex, PETG, Poly Vinyl Chloride and APET, for example. The thickness can range from 0.019 inches to 0.021 inches in one embodiment although the thickness may vary. In an embodiment, the thickness is 0.020 inches. The function of compression is to minimize variability in the thickness of the indicator strip material thereby controlling the volumetric uptake of blood.

The configuration of the device can be suited for the compressed indicator strip as follows. With reference again to FIG. 4, there are two openings in the layer 410. The first is a circular opening 413, which may be for example 0.5 inches in diameter. The second opening (the cut-out 412) is positioned distally relative to the first opening 413, and is in the shape of a dumbbell having a narrow rectangular midsection (such as on in a range of 0.25 inches wide and 0.75 inches long), with wide circular ends (such as having a diameter of around 0.5 inch). Unique to this embodiment, the indicator housing (i.e., layer 410) with the dumbbell-shaped cut-out 412 is constrained to a thickness equal to or slightly less than the nominal thickness of the indicator strip 215 (which may around 0.012 inches thick, for example) and is sandwiched between the top cover 405 and layer 415, thereby compressing the indicator strip 215 to a defined thickness. The proximal end of the dumbbell-shaped cut-out 412 opens downwardly towards the proximal hole 413 to provide a continuous space for the vertical separator 210 in layers 415 and 420 while maintaining face to face contact between the vertical separator 210 and the indicator strip 215. The vertical shaft descending down via the vertical separator 210 from the proximal end of the dumbbell shaped cut-out 412 is a half circle to full circle in shape, having a shared proximal surface from the dumbbell shaped cut-out 412. In an embodiment, this opening is slightly larger than a crescent or half moon at 0.35 inches long. The layer 410 (i.e., indicator housing) also serves to provide a minimal internal air space around the separation components, thereby minimizing the effects of humidity and other environmental variables on the blood migration characteristics in the device.

E. A Method and Device for Measuring Blood Parameters

Hematocrit refers to the packed cell volume of red blood cells and is measured as a percentage of total blood volume. A healthy person generally has a hematocrit of 45% (about 42 to 52% for men and about 36 to 48% for women). Anything below 42% for men and 36% for women is regarded as low hematocrit and referred to as anemia.

In the United States, over three million people are currently diagnosed with anemia. Many more are at risk of becoming anemic. Many conditions can lead to anemia. Common causes include chemotherapy or radiation therapy for cancer (which often suppresses the bone marrow's ability to regenerate blood cells), vitamin deficiencies (folate and vitamin B-12), and chronic inflammation. Causes also can be loss of blood from traumatic injury, surgery, or other sources of internal bleeding. While mild anemia often has no symptoms because the body can compensate for minor deficiencies in hematocrit, as anemia gets more severe, increased cardiac stress results. This can lead to tachycardia, shortness of breath, and headaches, and potentially coma and death.

As described herein, blood parameters commonly used in assessing anemia and other medical conditions include hematocrit and hemoglobin concentration. Hematocrit refers to the packed cell volume of red blood cells and is measured as a percentage of total blood volume. A healthy person generally has a hematocrit of 45% (about 42 to 52% for men and about 36 to 48% for women). Anything below 42% for men and 36% for women is regarded as low hematocrit and referred to as anemia. Hematocrit can be used in a determination of hemoglobin concentration.

Provided herein are methods and devices for determining blood parameters including hematocrit and/or hemoglobin concentration. Devices provided herein that can be used in the methods include one or more, or two or more, materials that is/are separation medium or media. The methods include application of a blood sample (typically a mammalian blood sample, such as a human or non-human mammal) to a separation medium, either directly or indirectly at a location that is in fluid communication with a separation medium and allowing the separation medium to become saturated with the blood sample. Devices provided herein can include surfaces or wells for receiving a blood sample that are in fluid communication with the separation medium. However, such a sample delivery well does not serve to meter or measure any particular volume of sample. Thus, particular embodiments of the device are meter-free. The volume of blood sample applied to the separation medium (either directly or through fluid communication with upstream elements, such as a well), is whatever unknown amount is delivered to the device. The volume only need be sufficient to saturate the separation medium, which can be determined visually.

Accordingly, amount of blood can be applied to the medium as long as the amount is in excess of the absorptive capacity of the separation medium (or the combined absorptive capacities of the separation media if more than one medium is used) in order for the medium to become saturated with the blood sample. The volume of the blood sample is not measured or metered and thus exact amount of blood applied to the medium does not need to be known or of a precise measurement.

The blood sample may be treated before and/or during migration in the separation medium. In a particular embodiment of the methods provided herein for determining hematocrit or hemoglobin concentration of a blood sample, an anticoagulant can be added to the fluid to prevent clotting of the blood sample. In particular devices provided herein, an anticoagulant may be located at one or more locations in the fluid path of the blood. In certain embodiments of the devices provided herein for determining blood parameters, a dye or other label may be placed at the distal end of the separation medium for purposes of confirming saturation of the complete separation medium. However, such a placement does not monitor liquid front movement prior to saturation of the medium. Dyes or labels to detectably mark the liquid front of the fluid are not included in the separation medium or any other portion of the fluid pathway, or are at least excluded from the separation zone of the separation medium. Thus, in particular embodiments of the devices provided herein, the separation medium, or the zone of separation of the separation medium, is free of any dyes or other substances that detectably mark the liquid front.

In a particular embodiment of the methods provided herein, separation of blood components is effected based on differential movement of blood components in a separation medium or media. Using such methods, blood cells, and, in particular, red blood cells, can be separated from the liquid component, such as plasma and/or serum, through fractional volume-dependent separation. That is, the migration distance of the red blood cells in the separation medium depends on the fractional volume of red blood cells in the whole blood. Because red blood cells of blood samples with different hematocrits migrate differently in the separation medium, it is possible to assess the volume of red blood cells in a blood sample and determine the percent volume of the cells relative to total blood volume using the methods and devices provided herein. The percent volume of red blood cells in blood is a measure of blood hematocrit.

Particular embodiments of the devices provided herein for determining blood hematocrit and/or hemoglobin concentrations include a porous separation medium that is any material that has a pore size capable of separating blood cells from plasma. Although red blood cells have an average diameter of 7-8 μm, they can deform such that the diameter is decreased. Thus, for example, suitable pore sizes of the medium for particular embodiments provided herein can be 1-8 μm in diameter, 1-5 μm in diameter or, in particular embodiments, 2-3 μm in diameter. The separation medium could also be any material made of packed beads or packed or woven fibers such that the effective pore size is suitable for separating blood cells from plasma.

Particular devices provided herein contain one or more separation media. In particular embodiments of the methods and devices, two separation media or more than two separation media are employed. The medium may be positioned such that fluid flow through it is normal (i.e., vertical) to the plane of the medium or within (i.e., horizontal or lateral) the plane of the medium. In a particular embodiment of the methods and devices provided herein, a single separation medium is positioned laterally with respect to the flow of fluid. In another embodiment of the methods and devices provided herein, two separation media are employed: (1) a first medium is placed so that fluid flow through it is vertical with respect to the plane of the medium, and (2) a second medium following, and in fluid communication with, the first medium wherein fluid flow through the second medium is lateral with respect to the plane of the medium. Typically, use of a vertically placed separation medium in the methods and devices provided herein is generally in addition to a horizontally placed separation medium and for the purpose of providing an initial gross separation of the component of interest from other components in the fluid mixture and/or staggering the presentation of the components of the fluid mixture to the lateral separation.

F. Examples

Example 1

Device Assembly

This example describes the assembly of an exemplary device having the features provided herein. In this exemplary device, the fluid is blood, the component or analyte is red blood cells that are separated from plasma using the device, and the assessed blood parameter is hematocrit, which is determined by measuring the migration of the red blood cells along the indicator strip once the strip is saturated with blood.

The exemplary device was assembled in order to obtain hematocrit values for various test subjects. The dimensions of the device were 0.787 inch×by 3.0 inches. The outer housing of the exemplary device was a rigid material (specifically, ABS, Sno White; Lustran 348-012002) that was solid on the bottom of the device and had an orifice on the top of the device for application of a blood sample into a proximal well. The inner components of the device are described below.

A. Proximal Bottom

The proximal bottom is a solid, thin, rigid material having an outer surface and an inner surface. Specifically, Rigid Poly Vinyl Chloride was used to construct the proximal bottom at a thickness of 0.01 inch. The outer surface of the proximal bottom provided the outer-facing, solid base of the device, whereas the opposite, or inner, surface provided the inner-facing bottom of the device. The inner-facing bottom served as a bottom of a volumetric capillary reservoir as well as provided a surface for the blood sample to be applied. The blood sample application area of the inner surface of the proximal bottom was coated with a 20 □l solution of 70% ethanol containing 195 U/ml of Heparin sodium salt (to inhibit clotting of the blood sample) and a mild 0.3% Tween-20® solution to promote migration of blood into the volumetric capillary reservoir.

B. Proximal Housing

The proximal housing is a thin, rigid material. Specifically, Rigid Poly Vinyl Chloride was used to construct the proximal housing at a thickness of 0.02 inch. The size and shape of the proximal housing were the same as those of the proximal bottom. There was a hole in the proximal housing in the shape of a 0.576 inch long center to center tear drop with the 0.5 inch diameter wide end of the tear drop positioned proximally compared to the position of the 0.12 inch diameter narrow end of the tear drop. The proximal housing was adhered to the proximal bottom using 3M's 467 MP 2.3 mil. adhesive transfer tape. Once adhered to the proximal bottom, the edges of the hole in the proximal housing provided the walls of a volumetric capillary reservoir and set the volume for the reservoir at 0.002 cubic inches (33 □l). The wide, circular end of the tear drop shape of the reservoir also served as the blood delivery reservoir. The edges of the reservoir and the portion of the proximal cover that capped the volumetric capillary reservoir were together coated with a 10 □l solution of 70% ethanol containing 195 U/ml Heparin sodium salt to inhibit clotting of the blood sample and a mild 0.3% Tween-20® solution to promote migration of blood into the volumetric capillary reservoir.

C. Proximal Cover

The proximal cover is a thin, rigid material. Specifically, Rigid Poly Vinyl Chloride was used to construct the proximal cover at a thickness of 0.01 inch. The size and shape of the proximal cover were the same as those of the proximal housing. There were two holes in the proximal cover. One hole was circular in the shape measuring 0.5 inches in diameter and was positioned proximally with respect to the second hole, which was 0.125 inches in diameter. The proximal cover was adhered to the proximal housing 3M's 467 MP 2.3 mil. adhesive transfer tape such that the larger, proximal, circular hole was positioned over the wide, circular end of the tear drop shape of the reservoir formed by the proximal housing. Once adhered, the proximal cover capped the volumetric capillary reservoir, leaving a circular opening for the blood sample delivery reservoir. The smaller, distal circular hole in the proximal cover provided the distal exit orifice of the volumetric capillary reservoir. The distal exit orifice was sized and located to promote capillary wicking of blood into the vertical separator. As mentioned above, the portion of the proximal cover that capped the volumetric capillary reservoir and edges of the reservoir were together coated with a 10 □l solution of 70% ethanol containing 195 U/ml of Heparin sodium salt to inhibit clotting of the blood sample and a mild 0.3% Tween-20® solution to promote migration of blood into the volumetric capillary reservoir.

D. Vertical Separator

The vertical separator is a glass fiber filter. Specifically, Millipore AP25 glass fiber filters with binder resin with the following specifications were used: 2.0 μm pore size; 1200 μm thickness; 5.8 mL/min/cm² water flow rate; 35 mm of H₂0 @ 10.5 fpm or 5.3 cm/s air resistance; 63.6 L/min/cm² @ 10 psi air flow; 0.03% DOP penetration at 10.5 FPM; 110 μg/cm² protein binding; and 140 g/m² weight. A semicircle shape was used to make the distance from any point on the distal edge of the vertical pad and the proximal edge of the resolving region of the indicator strip consistent. This promoted the blood front to converge at the resolving region of the indicator strip. The vertical separator was adhered to the proximal cover using 3M's 467 MP 2.3 mil. adhesive transfer tape and situated directly above the distal exit orifice. The vertical separator was positioned perpendicular to the plane of the housing. The distal orifice controlled blood flow such that blood could only enter the indicator housing via capillary action of the indicator strip and, therefore, was unable to flow around and avoid being properly resolved within the indicator strip.

E. Indicator Housing

The indicator housing is a thin, rigid material. Specifically, Rigid Poly Vinyl Chloride was used to construct the indicator housing at a thickness of 0.04 inch. The size and shape of the indicator housing were the same as those of the proximal cover. There were two holes in the indicator housing. One hole was circular in shape measuring 0.5 inches in diameter and was positioned proximally with respect to the second hole. The second hole was in the shape of a dumbbell having a narrow rectangular midsection measuring 0.25 inches wide and 0.75 inches long with 0.5 inch diameter wide circular ends. The indicator housing was adhered to the proximal cover using 3M's 467 MP 2.3 mil. adhesive transfer tape such that the circular proximal hole in the housing was positioned directly above the circular proximal hole in the proximal cover. In positioning the indicator housing in this way, the vertical separator was located in, and perpendicular to the plane of, the proximal wide circular end of the dumbbell-shaped hole. The indicator housing provided a minimal internal volume around the separation components. This prevented humidity and other environmental variables from affecting blood migration characteristics in the device.

F. Indicator Strip

The indicator strip is a lateral blood separator made of thin glass-fiber material. Specifically, MF1 glass-fiber from Whatman was used. This is a polyvinyl alcohol-bound glass fiber filter that can remove particles greater than 2 μm. The shape of the strip was that of a dumbbell having a narrow rectangular midsection and wide circular ends, following the shape of the second hole of the indicator housing. The overall size of the strip was somewhat smaller than that of the second 0.5 inch diameter hole of the indicator housing. Using 3M's 467 MP 2.3 mil. adhesive transfer tape, the indicator strip was adhered to the bottom surface of the distal top which, as described herein, also forms the top of the device with its outer, top surface. The distal top, with the indicator strip adhered to its bottom surface, was adhered using 3M's 467 MP 2.3 mil. adhesive transfer tape to the indicator housing such that the indicator strip was positioned within the second (dumbbell-shaped) hole of the indicator housing thereby creating a sealed internal volume housing the indicator strip. The indicator strip was thus contained in a space wherein the bottom, or floor, of the space provided by the proximal cover served as a base for the strip, the dumbbell-shaped hole in the indicator housing provided the walls of the space around the strip and the bottom surface of the distal top provided the roof of the space. The most proximal semicircle half of the proximal wide end of the indicator strip was situated above and in contact with the top of the vertical separator which was adhered on the proximal cover. Blood separation along the indicator strip provided resolution, based on hematocrit, and could be visibly measured. The distal pad of the indicator strip provided a sink for excess plasma so that the blood plasma interface stabilized along the indicator strip.

Dry bromophenol blue (BPB) was solubilized into 95% ethanol at 10 mg/ml [weight-to-volume (w/v)]. 2 μl of this solution was applied onto the center of the distal pad of the indicator strip and allowed to dry for 5 minutes. The blue color provided a visual indicator that plasma successfully migrated to the distal pad of the indicator strip, indicating successful migration of plasma through the strip.

G. Distal Top

The distal top is a thin rigid transparent material. Specifically, Rigid Poly Vinyl Chloride was used to construct the distal top at a thickness of 0.01 inch. The size and shape of the distal top were the same as those of the indicator housing. The distal top contained a circular 0.02 inch diameter hole at the distal end of the indicator housing dumb-bell which served as an air escape opening allowing displaced air to escape as blood was drawn into the device. One surface of the distal top formed the top of the device facing the exterior. Using 3M's 467 MP 2.3 mil. adhesive transfer tape, the indicator strip was adhered to the opposite (or bottom) surface of the distal top such that the narrow rectangular portion of the indicator strip aligned with the narrow rectangular transparent portion of the distal top and the proximal and distal windows aligned with the proximal and distal wide ends of the indicator strip, respectively. The windows facilitated visual observation of the presence of sufficient blood sample reaching the proximal end of the indicator strip and of successful migration of plasma through the strip. Using 3M's 467 MP 2.3 mil. adhesive transfer tape, the thus-formed distal top/indicator strip element was adhered to the top surface of the indicator house such that the indicator strip was positioned within the second (dumbbell-shaped) hole of the indicator housing thereby creating a sealed internal volume housing the indicator strip.

The outer-facing surface of the distal top was printed with graphics indicating the function of the device.

H. Design Specifications

The exemplary device described in this example was generated with the design specifications as outlined in Table 1 below.

TABLE 1

| Device Design Specifications | | |
|---|---|---|
| Specification | Desired | Required |
| Resolution | 4 mm per g/dL Hgb | 3 mm per g/dL Hgb |
| Read Error | ±0.5 mm | ±1 mm |
| Device Error | ±0.5 g/dL | ±1.0 g/dL |
| Registration Error | ±0.5 mm | ±1 mm |
| Cleanliness Rating | Aseptic Blood Capture Area | |
| Temperature range during test | | 20-35° |
| Temperature range shipping | | −20-50° |
| Target Stability | 1 year @ 25° | |
| Humidity range (storage & use) | | 10-100% |

TABLE 1-continued

Device Design Specifications

| Specification | Desired | Required |
|---|---|---|
| Pressure Range | | 19-32 in Hg |
| Minimum Read Time | 10 minutes | 15 minutes |
| Maximum Read Time | >14 days | |
| Minimum Blood Volume | 50 µl | |
| Hb Range | 7-13 g/dL | |

Calibration of the Exemplary Device:

For the exemplary device that includes a proximal lobe with a radius of 4.6 mm and a distal lobe with a radius of 4.4 mm, and an indicator region having a width of 1.1 mm and length of 20 mm, the areas of the proximal and distal lobes are 56.7 mm² and 60.8 mm² respectively. The total area of the strip is thus 139.5 mm². The vertical separator has an area of 10 mm². The liquid volume per area of the strip is 0.4 ul/mm², and 1.25 ul/mm² for the vertical separator. We have found the separation efficiency R to be 0.58. From Equation 4:

$$H_{min} = 1 - \frac{(20)(1.1) + 60.8}{0.58\left(10\left(\frac{1.25}{0.4}\right) + 139.5\right)} = 16.4\%$$

$$H_{max} = 1 - \frac{60.8}{0.58\left(10\left(\frac{1.25}{0.4}\right) + 139.5\right)} = 38.7\%$$

$$\text{resolution} = \frac{0.58\left(10\left(\frac{1.25}{0.4}\right) + 139.5\right)}{1.1} = 90 \text{ mm} = 0.90 \frac{\text{mm}}{\% H}$$

Example 2

Device Trial Usage

In this example, the exemplary device described in Example 1 was used to determine hematocrit values of two test subjects: subject 1 and subject 2. A side-by-side comparison of two devices was performed. Both devices were identical, with the exception that the device for subject 2 did not contain bromophenol blue on the distal end of the indicator strip (see FIG. 5). Two drops (approx. 50 µl) of venous blood from each subject was applied to the respective devices. The indicator window on each device properly turned red, indicating that enough blood was administered. In addition, the device used by subject 1 turned blue at the distal end of the indicator strip, indicating that the test ran appropriately having achieved saturation and the hematocrit could be read. Since bromophenol blue was not applied to the device used by subject 2, the distal end of the indicator strip for this device remained colorless. Therefore, saturation was estimated by visualizing the presence of plasma within the distal pad. For each subject's device, hematocrit was read at 10 minutes. The indicator strip measured the hematocrit at 52% for test subject 1 and 50% for subject 2. This was consistent with prior laboratory hematocrit tests for the subjects' blood. The results indicated that the red blood cell front arrested along the indicator strip in both tests based on each test subject's percent hematocrit. Specifically, the lower hematocrit sample from subject 2 showed less migration of the red blood cell front than that of the higher hematocrit sample from subject 1.

Example 3

Comparison of Methods Used to Determine Hematocrit

In this example, samples were tested for hematocrit values using a standard spun capillary tube measurement and compared to samples measured by the exemplary device described herein.

A. Hematocrit and Hemoglobin Measurement Precision

In this experiment, 30 venous blood samples were selected based on % hematocrit as determined by the standard spun capillary tube measurement technique (described in Bull B S, Koepke J A, Simson E et al. Procedure for determining packed cell volume by the hematocrit method. Third edition. NCCLS publication H7-A3. Wayne, Pa.: NCCLS, 2000). Specifically, whole blood (75 ml) was gently pipetted into the spun hematocrit tube [Drummond Hemato-Cald tubes (Cat#1-000-7500-HC)]. The bottom of the tube was sealed with Critoseal [McCormick Scientific (Cat#215003)]. Tubes were centrifuged at 3000 rpm in the Silencer Centrifuge H-20 for 10 minutes at RT. Tubes were immediately collected upon completion of the spin and measured. Measurements of the total combined height of the packed blood and plasma, and the height of the packed red blood cells alone were determined using calipers and recorded. Percent hematocrit (% HCT) was calculated as the ratio of the height of the packed cells (mm) over the total height (mm). The samples were divided into three groups of ten based on % HCT: one group at 26% HCT, a second group at 36% HCT and a third group at 41% HCT.

For each group, individual blood samples were tested for % HCT using the exemplary device described in Example 1 with the method described in Example 2. For each sample, red blood cell (RBC) migration distance was measured (in mm) using a ruler and a mean value for distance and standard deviation were calculated for each HCT group. HCT values based on measurements read on the device were obtained for each sample and a mean value for % HCT and standard deviation were calculated for each HCT group.

Hemoglobin (Hb) levels (in g/dL) also were obtained for each sample and a mean value for Hb levels and standard deviation were calculated for each HCT group. Hb levels were determined using a standard conversion formula.

HCT (%) = (0.03 × Hb (g/dL) + 0.0083) × 100

The Table below provides data comparing % hematocrit values obtained using the spun capillary method (first column on the left) vs. the instant device described herein (fourth column from the left).

TABLE 2

Hematocrit (HCT) and Hemoglobin (Hb) Measurements

| Spun Capillary HCT (%) | Mean RBC Migration Distance in instant device (mm) | Standard Deviation RBC Migration Distance in instant device (mm) | Mean Calculated HCT (%) in instant device | Standard Deviation Calculated HCT (%) in instant device | Mean Calculated Hb (g/dL) in instant device | Standard Deviation Calculated Hb (g/dL) in instant device | % CV in instant device |
|---|---|---|---|---|---|---|---|
| 26 (n = 10) | 6.1 | 0.84 | 25 | 0.97 | 8.5 | 0.32 | 3.8 |
| 36 (n = 10) | 15.5 | 0.85 | 36 | 0.98 | 12.1 | 0.33 | 2.7 |
| 41 (n = 10) | 18.7 | 0.97 | 40 | 1.1 | 13.3 | 0.37 | 2.8 |

For RBC migration distance, values obtained for standard deviation indicate consistent RBC migration distances within each HCT group. For % HCT, the mean HCT value obtained for group 1 was 25 (vs. 26 for the spun capillary HCT); for group 2 was 36 (vs. 36 for the spun capillary method); and for group 3 was 40 (vs. 41 for the spun capillary method). Thus the HCT values obtained using the instant device were identical or nearly identical to those obtained using the standard spun capillary method. Further, the values obtained for standard deviation indicate consistent readings within each HCT group. For Hb levels, values obtained for standard deviation indicate consistent measurements of Hb within each HCT group.

B. Hematocrit Measurement Correlation

In this experiment, 68 blood samples were each tested for hematocrit values using spun capillary tubes and the device described herein. Hemoglobin levels also were derived based on these measurements using the HCT to Hb conversion formula (presented above). The hematocrit values in the samples used ranged from 20% to 41% and the hemoglobin levels ranged from 6.7 g/dL to 13.7 g/dL. The hematocrit value data for these samples is presented in Table $$ below.

TABLE 3

Hematocrit Measurement Correlation

| Sample Number | Spun HCT (%) | Device HCT (%) |
|---|---|---|
| 1 | 26 | 29 |
| 2 | 30 | 31 |
| 3 | 36 | 36 |
| 4 | 40 | 40 |
| 5 | 26 | 26 |
| 6 | 30 | 30 |
| 7 | 36 | 36 |
| 8 | 40 | 41 |
| 9 | 20 | 23 |
| 10 | 24 | 26 |
| 11 | 31 | 31 |
| 12 | 35 | 37 |
| 13 | 40 | 43 |
| 14 | 20 | 23 |
| 15 | 24 | 25 |
| 16 | 31 | 32 |
| 17 | 35 | 37 |
| 18 | 40 | 43 |
| 19 | 20 | 18 |
| 20 | 25 | 21 |
| 21 | 30 | 29 |
| 22 | 35 | 33 |
| 23 | 40 | 40 |
| 24 | 20 | 18 |
| 25 | 25 | 23 |
| 26 | 30 | 29 |
| 27 | 35 | 32 |
| 28 | 40 | 39 |
| 29 | 21 | 22 |
| 30 | 26 | 26 |
| 31 | 30 | 30 |
| 32 | 36 | 35 |
| 33 | 40 | 43 |
| 34 | 21 | 22 |
| 35 | 26 | 25 |
| 36 | 30 | 31 |
| 37 | 36 | 36 |
| 38 | 40 | 42 |
| 39 | 26 | 25 |
| 40 | 26 | 28 |
| 41 | 26 | 25 |
| 42 | 26 | 25 |
| 43 | 26 | 24 |
| 44 | 26 | 25 |
| 45 | 26 | 25 |
| 46 | 26 | 26 |
| 47 | 26 | 25 |
| 48 | 26 | 25 |
| 49 | 36 | 36 |
| 50 | 36 | 36 |
| 51 | 36 | 37 |
| 52 | 36 | 35 |
| 53 | 36 | 38 |
| 54 | 36 | 37 |
| 55 | 36 | 37 |
| 56 | 36 | 36 |
| 57 | 36 | 35 |
| 58 | 36 | 36 |
| 59 | 41 | 40 |
| 60 | 41 | 39 |
| 61 | 41 | 41 |
| 62 | 41 | 42 |
| 63 | 41 | 41 |
| 64 | 41 | 41 |
| 65 | 41 | 39 |
| 66 | 41 | 39 |
| 67 | 41 | 40 |
| 68 | 41 | 39 |

The data in Table 3 shows a strong correlation between the HCT values obtained via a standard spun capillary tube method and the device described herein. A correlation coefficient of 0.975 was calculated using a standard equation. Specifically, $$\text{Correlation}(r) = N\Sigma XY - (\Sigma X)(\Sigma Y)/\sqrt{([N\Sigma X^2 - (\Sigma X)^2][N\Sigma Y^2 - (\Sigma Y)^2])}$$

where:
 N=Number of samples
 X=Spun Capillary HCT value
 Y=Device HCT value
 ΣXY=Sum of the product of spun HCT and device HCT values
 ΣX=Sum of spun HCT values
 ΣY=Sum of device HCT values
 $\Sigma X^2$=Sum of square spun HCT values
 $\Sigma Y^2$=Sum of square device HCT values The ratio of HCT value generated from the instant device versus the HCT value generated from spun capillary tubes was calculated for each test subject. The results of these calculations are set forth in TABLE $$ below.

TABLE 4

Instant Device Vs. Spun HCT Ratio Distribution

| Instant Device Vs. Spun HCT Ratio | % of Test Population |
| --- | --- |
| 0.81-0.85 | 1 |
| 0.86-0.90 | 3 |
| 0.91-0.95 | 9 |
| 0.96-1.0 | 34 |
| 1.01-1.05 | 37 |
| 1.06-1.10 | 12 |
| 1.11-1.15 | 4 |

The narrow bell-shaped distribution of HCT value ratios set forth in TABLE 4 above indicates that HCT values obtained for most test subjects were nearly identical for both HCT measurements administered. Thus, the instant device generated reliable results that were similar or identical to the measurements generated by a standard spun capillary tube method.

Example 4

Comparison of Methods Used to Determine Hemoglobin Levels

In this example, samples were tested for hemoglobin values using the Hemocue® hemoglobin analyzer device and compared to samples measured by the device described herein. 200 blood samples were each tested for hemoglobin values using a Hemocue® device (following manufacturer's instructions) and the device described herein (using the method described in Example 2). The hemoglobin value data for 200 samples is presented in Table 5 below.

TABLE 5

Hemoglobin Measurement Correlation

| Sample Number | Hb (g/dL) Hemocue® | Device Hb (g/dL) |
| --- | --- | --- |
| 1 | 8.35 | 7.89 |
| 2 | 8.35 | 7.89 |
| 3 | 8.35 | 7.89 |
| 4 | 8.35 | 7.89 |
| 5 | 8.35 | 7.89 |
| 6 | 8.35 | 7.89 |
| 7 | 8.35 | 7.89 |
| 8 | 8.35 | 7.89 |
| 9 | 8.35 | 7.89 |
| 10 | 8.35 | 7.89 |
| 11 | 8.45 | 8.69 |
| 12 | 8.45 | 8.58 |
| 13 | 8.45 | 8.35 |
| 14 | 8.45 | 8.35 |
| 15 | 8.45 | 8.58 |
| 16 | 8.45 | 8.35 |
| 17 | 8.45 | 8.58 |
| 18 | 8.45 | 8.46 |
| 19 | 8.45 | 8.35 |
| 20 | 8.45 | 8.23 |
| 21 | 8.60 | 8.12 |
| 22 | 8.60 | 8.23 |
| 23 | 8.60 | 8.35 |
| 24 | 8.60 | 8.23 |
| 25 | 8.60 | 8.35 |
| 26 | 8.60 | 8.23 |
| 27 | 8.60 | 8.00 |
| 28 | 8.60 | 8.35 |
| 29 | 8.60 | 7.89 |
| 30 | 8.60 | 8.12 |
| 31 | 8.95 | 9.04 |
| 32 | 8.95 | 9.27 |
| 33 | 8.95 | 9.50 |
| 34 | 8.95 | 9.04 |
| 35 | 8.95 | 8.92 |
| 36 | 8.95 | 8.81 |
| 37 | 8.95 | 9.04 |
| 38 | 8.95 | 9.04 |
| 39 | 8.95 | 9.04 |
| 40 | 8.95 | 9.04 |
| 41 | 9.35 | 9.73 |
| 42 | 9.35 | 9.84 |
| 43 | 9.35 | 9.73 |
| 44 | 9.35 | 9.73 |
| 45 | 9.35 | 9.61 |
| 46 | 9.35 | 9.61 |
| 47 | 9.35 | 9.84 |
| 48 | 9.35 | 9.50 |
| 49 | 9.35 | 9.73 |
| 50 | 9.35 | 9.61 |
| 51 | 9.60 | 9.73 |
| 52 | 9.60 | 9.73 |
| 53 | 9.60 | 9.50 |
| 54 | 9.60 | 9.50 |
| 55 | 9.60 | 9.50 |
| 56 | 9.60 | 9.04 |
| 57 | 9.60 | 9.50 |
| 58 | 9.60 | 9.50 |
| 59 | 9.60 | 9.27 |
| 60 | 9.60 | 8.81 |
| 61 | 9.60 | 9.38 |
| 62 | 9.60 | 9.27 |
| 63 | 9.60 | 9.50 |
| 64 | 9.60 | 9.27 |
| 65 | 9.60 | 9.38 |
| 66 | 9.60 | 9.15 |
| 67 | 9.60 | 9.04 |
| 68 | 9.60 | 9.27 |
| 69 | 9.60 | 9.27 |
| 70 | 9.60 | 9.15 |
| 71 | 9.60 | 9.61 |
| 72 | 9.60 | 10.19 |
| 73 | 9.60 | 9.73 |
| 74 | 9.60 | 9.50 |
| 75 | 9.60 | 9.27 |
| 76 | 9.60 | 9.84 |
| 77 | 9.60 | 9.50 |
| 78 | 9.60 | 10.07 |
| 79 | 9.60 | 9.73 |
| 80 | 9.60 | 9.27 |
| 81 | 9.80 | 9.73 |

TABLE 5-continued

Hemoglobin Measurement Correlation

| Sample Number | Hb (g/dL) Hemocue ® | Device Hb (g/dL) |
|---|---|---|
| 82 | 9.80 | 10.65 |
| 83 | 9.80 | 10.42 |
| 84 | 9.80 | 9.96 |
| 85 | 9.80 | 9.73 |
| 86 | 9.80 | 10.19 |
| 87 | 9.80 | 10.30 |
| 88 | 9.80 | 9.73 |
| 89 | 9.80 | 9.96 |
| 90 | 9.80 | 9.84 |
| 91 | 10.10 | 9.73 |
| 92 | 10.10 | 9.84 |
| 93 | 10.10 | 9.96 |
| 94 | 10.10 | 9.84 |
| 95 | 10.10 | 9.73 |
| 96 | 10.10 | 9.84 |
| 97 | 10.10 | 9.38 |
| 98 | 10.10 | 9.50 |
| 99 | 10.10 | 9.50 |
| 100 | 10.10 | 9.50 |
| 101 | 10.15 | 9.96 |
| 102 | 10.15 | 9.73 |
| 103 | 10.15 | 9.73 |
| 104 | 10.15 | 9.73 |
| 105 | 10.15 | 9.73 |
| 106 | 10.15 | 9.91 |
| 107 | 10.15 | 9.61 |
| 108 | 10.15 | 9.61 |
| 109 | 10.15 | 9.50 |
| 110 | 10.15 | 9.50 |
| 111 | 10.25 | 10.07 |
| 112 | 10.25 | 9.96 |
| 113 | 10.25 | 10.30 |
| 114 | 10.25 | 9.96 |
| 115 | 10.25 | 10.07 |
| 116 | 10.25 | 9.96 |
| 117 | 10.25 | 9.73 |
| 118 | 10.25 | 9.84 |
| 119 | 10.25 | 9.61 |
| 120 | 10.25 | 10.19 |
| 121 | 10.35 | 10.30 |
| 122 | 10.35 | 10.99 |
| 123 | 10.35 | 10.42 |
| 124 | 10.35 | 10.42 |
| 125 | 10.35 | 10.65 |
| 126 | 10.35 | 10.42 |
| 127 | 10.35 | 10.53 |
| 128 | 10.35 | 10.53 |
| 129 | 10.35 | 10.42 |
| 130 | 10.35 | 10.42 |
| 131 | 10.40 | 10.30 |
| 132 | 10.40 | 10.76 |
| 133 | 10.40 | 10.42 |
| 134 | 10.40 | 10.30 |
| 135 | 10.40 | 10.42 |
| 136 | 10.40 | 10.53 |
| 137 | 10.40 | 10.30 |
| 138 | 10.40 | 10.19 |
| 139 | 10.40 | 10.19 |
| 140 | 10.40 | 9.96 |
| 141 | 10.60 | 10.88 |
| 142 | 10.60 | 11.10 |
| 143 | 10.60 | 10.88 |
| 144 | 10.60 | 10.65 |
| 145 | 10.60 | 11.33 |
| 146 | 10.60 | 11.45 |
| 147 | 10.60 | 10.65 |
| 148 | 10.60 | 10.99 |
| 149 | 10.60 | 10.88 |
| 150 | 10.60 | 10.99 |
| 151 | 10.65 | 10.88 |
| 152 | 10.65 | 10.65 |
| 153 | 10.65 | 10.99 |
| 154 | 10.65 | 10.65 |
| 155 | 10.65 | 10.99 |
| 156 | 10.65 | 10.65 |
| 157 | 10.65 | 10.88 |
| 158 | 10.65 | 10.65 |
| 159 | 10.65 | 10.76 |
| 160 | 10.65 | 10.88 |
| 161 | 11.50 | 11.22 |
| 162 | 11.50 | 11.10 |
| 163 | 11.50 | 11.33 |
| 164 | 11.50 | 11.56 |
| 165 | 11.50 | 11.10 |
| 166 | 11.50 | 11.33 |
| 167 | 11.50 | 11.22 |
| 168 | 11.50 | 10.99 |
| 169 | 11.50 | 11.22 |
| 170 | 11.50 | 11.22 |
| 171 | 11.60 | 11.79 |
| 172 | 11.60 | 12.02 |
| 173 | 11.60 | 11.91 |
| 174 | 11.60 | 11.79 |
| 175 | 11.60 | 11.33 |
| 176 | 11.60 | 11.45 |
| 177 | 11.60 | 11.56 |
| 178 | 11.60 | 11.45 |
| 179 | 11.60 | 11.45 |
| 180 | 11.60 | 11.45 |
| 181 | 11.65 | 11.68 |
| 182 | 11.65 | 11.68 |
| 183 | 11.65 | 12.14 |
| 184 | 11.65 | 11.79 |
| 185 | 11.65 | 11.56 |
| 186 | 11.65 | 11.79 |
| 187 | 11.65 | 11.91 |
| 188 | 11.65 | 11.79 |
| 189 | 11.65 | 11.79 |
| 190 | 11.65 | 11.68 |
| 191 | 11.75 | 11.79 |
| 192 | 11.75 | 12.02 |
| 193 | 11.75 | 11.79 |
| 194 | 11.75 | 11.79 |
| 195 | 11.75 | 11.79 |
| 196 | 11.75 | 11.79 |
| 197 | 11.75 | 11.91 |
| 198 | 11.75 | 11.79 |
| 199 | 11.75 | 12.02 |
| 200 | 11.75 | 11.79 |

The data in Table 5 shows a strong correlation between the hemoglobin values obtained via a Hemocue® device and the device described herein. A correlation coefficient of 0.96 was calculated using a standard equation. Specifically, $$\text{Correlation}(r) = N\Sigma XY - (\Sigma X)(\Sigma Y)/\sqrt{([N\Sigma X^2 - (\Sigma X)^2][N\Sigma Y^2 - (\Sigma Y)^2])}$$

where:
N=Number of samples
X=Hb (g/dL) Hemocue® value
Y=Device Hb (g/dL) value
$\Sigma XY$=Sum of the product of Hb Hemocue® value and device Hb value
$\Sigma X$=Sum of Hb Hemocue® value
$\Sigma Y$=Sum of device Hb values
$\Sigma X^2$=Sum of square Hb Hemocue® value
$\Sigma Y^2$=Sum of square device Hb values Since modifications will be apparent to those of skill in this art, it is intended that this invention be limited only by the scope of the appended claims.

The invention claimed is:

1. A method of determining hematocrit using a lateral flow indicator strip substrate, comprising:
 (a) applying blood to a sample well communicating with a capillary reservoir communicating with a vertical separator communicating with a proximal end of a lateral flow indicator strip substrate, wherein the vertical separator is positioned such that the blood applied to the sample well is vertically separated and can only enter the lateral flow indicator strip substrate via capillary action from the capillary reservoir and wherein the lateral flow indicator strip substrate provides for differential migration of the red blood cells and the plasma from the blood in the lateral flow indicator strip substrate;

(b) allowing the blood to saturate the lateral flow indicator strip substrate; and (c) determining the hematocrit of the applied blood using premarked concentration values of the red blood cells based on the position of migration of the red blood cells in the lateral flow indicator strip substrate relative to the proximal or distal end of the lateral flow indicator strip substrate, wherein the position of migration of the red blood cells is directly proportional to hematocrit;

wherein the amount of blood applied in step (a) is not metered, not known and is not measured but is in an amount sufficient to saturate the lateral flow indicator strip substrate; and, wherein dyes or labels to detectably mark the fluid or liquid front of the blood are not included in the blood or lateral flow indicator strip substrate.

2. The method of claim 1, wherein the blood is obtained from a human subject.

3. The method of claim 2, wherein the blood is applied directly from the human subject into the sample well for direct communication to the capillary reservoir and vertical separator onto the lateral flow indicator strip substrate.

4. The method of claim 2, wherein the blood is collected from the human subject prior to being applied to the substrate.

5. The method of claim 1, wherein the blood is from a stored container.

6. The method of claim 2, wherein the human subject is in the home, in a hospital emergency room, in a hospital operating room, in a hospital laboratory, in a clinical laboratory, in a doctor's offices or outside.

7. The method of claim 1, wherein the position of migration of the red blood cells in the lateral flow indicator strip substrate is determined relative to the proximal end of the lateral flow indicator strip substrate.

8. The method of claim 1, wherein the lateral flow indicator strip substrate is a glass fiber filter strip.

9. The method of claim 8, wherein the proximal and distal ends of the glass fiber filter strip are wider than the midsection of the glass fiber filter strip.

10. The method of claim 9, wherein the glass fiber filter strip is shaped like a dumbbell.

11. The method of claim 10, wherein dimensions of the proximal and distal ends of the dumbbell are adjusted whereby, upon, the position of migration of the red blood cells is in the midsection of the glass fiber filter strip.

* * * * *